United States Patent [19]
Adams

[11] Patent Number: 5,965,093
[45] Date of Patent: *Oct. 12, 1999

[54] DECONTAMINATION SYSTEM WITH IMPROVED COMPONENTS

[75] Inventor: Billy J. Adams, Usk, Wash.

[73] Assignee: Amphion International, Limited, Dublin, Ireland

[*] Notice: This patent is subject to a terminal disclaimer.

[21] Appl. No.: 08/750,443

[22] PCT Filed: Jul. 7, 1995

[86] PCT No.: PCT/US95/08506

§ 371 Date: Dec. 6, 1996

§ 102(e) Date: Dec. 6, 1996

[87] PCT Pub. No.: WO96/01791

PCT Pub. Date: Jan. 25, 1996

Related U.S. Application Data

[63] Continuation-in-part of application No. 08/273,102, Jul. 8, 1994, Pat. No. 5,466,425.

[51] Int. Cl.$^6$ .............................. C02F 1/30; C02F 1/32; C02F 1/36; C02F 1/48

[52] U.S. Cl. .................. 422/186.04; 422/20; 422/22; 422/24; 422/127; 422/128; 422/186; 422/186.3; 422/900; 422/907

[58] Field of Search ........................... 422/20, 22, 24, 422/186, 186.04, 186.3, 900, 907, 127, 128; 210/243, 748

[56] References Cited

U.S. PATENT DOCUMENTS

| | | |
|---|---|---|
| 2,122,741 | 7/1938 | Haddad . |
| 3,336,220 | 8/1967 | Neidi . |
| 3,617,178 | 11/1971 | Clouston . |
| 3,672,823 | 6/1972 | Boucher . |
| 3,725,226 | 4/1973 | Stoner . |
| 3,753,886 | 8/1973 | Myers . |
| 4,013,552 | 3/1977 | Kreuter . |
| 4,066,544 | 1/1978 | Stark . |
| 4,123,339 | 10/1978 | Gale et al. . |
| 4,179,616 | 12/1979 | Coviello et al. . |
| 4,214,962 | 7/1980 | Pincon . |
| 4,336,223 | 6/1982 | Hillman . |
| 4,384,943 | 5/1983 | Stoner et al. . |
| 4,400,270 | 8/1983 | Hillman . |
| 4,458,153 | 7/1984 | Wesley . |
| 4,471,225 | 9/1984 | Hillman . |
| 4,494,357 | 1/1985 | DiGeronimo . |
| 4,524,079 | 6/1985 | Hofmann . |
| 4,548,716 | 10/1985 | Boeve . |
| 4,561,953 | 12/1985 | Buralidhara et al. . |
| 4,656,813 | 4/1987 | Baldini et al. . |
| 4,719,018 | 1/1988 | Przybylski . |
| 4,728,368 | 3/1988 | Pedziwiatr . |
| 4,752,401 | 6/1988 | Bodenstein . |

(List continued on next page.)

FOREIGN PATENT DOCUMENTS

| | | |
|---|---|---|
| 3117307 | 6/1980 | Germany . |
| 5-237479 | 5/1993 | Japan . |
| WO 95/09815 | 4/1995 | WIPO . |

*Primary Examiner*—Daniel J. Jenkins
*Attorney, Agent, or Firm*—Darby & Darby

[57] ABSTRACT

A system for reducing biological organisms in a liquid effluent to no-viable organic molecules that includes: a stunning chamber (38) that applies a voltage potential across biological organisms to break cell membranes and disable the defense mechanisms of viral organisms to ultraviolet radiation; a cavitation chamber (86) to physically destroy any remaining membranes of biologicals in the effluent that may play host to viral organisms or allow such to hide therein, the action of the stunning and cavitation chambers releasing interferons; and a molecularly implanted stimulated emitter (MISE) chamber (108) in which high levels of ultraviolet radiation and electromagnetic energy are applied to virions and spores that remain at frequencies that are readily absorbed and operate to dissociate any viable DNA and RNA strands remaining, to thereby cause "death". The resulting effluent is pulsed through the stunning, cavitation, and MISE chambers to gain maximum effect thereof.

39 Claims, 11 Drawing Sheets

U.S. PATENT DOCUMENTS

| | | |
|---|---|---|
| 4,759,849 | 7/1988 | Baumann et al. . |
| 4,766,321 | 8/1988 | Lew et al. . |
| 4,808,287 | 2/1989 | Hark . |
| 4,836,929 | 6/1989 | Baumann et al. . |
| 4,857,204 | 8/1989 | Joklik . |
| 4,872,959 | 10/1989 | Herbst et al. . |
| 4,906,387 | 3/1990 | Pisani . |
| 4,917,782 | 4/1990 | Davies . |
| 4,957,606 | 9/1990 | Juvan . |
| 4,961,860 | 10/1990 | Masri . |
| 4,963,750 | 10/1990 | Wilson . |
| 4,990,260 | 2/1991 | Pisani . |
| 5,026,477 | 6/1991 | Yen . |
| 5,026,564 | 6/1991 | Hayden . |
| 5,049,400 | 9/1991 | Hayden . |
| 5,091,152 | 2/1992 | Thomas, Sr. . |
| 5,120,450 | 6/1992 | Stanley, Jr. . |
| 5,130,031 | 7/1992 | Johnston . |
| 5,130,032 | 7/1992 | Sartori . |
| 5,198,122 | 3/1993 | Koszalka et al. ........................ 219/748 |
| 5,217,607 | 6/1993 | Dalton, III et al. . |
| 5,240,618 | 8/1993 | Caldwell et al. . |
| 5,247,178 | 9/1993 | Ury et al. . |
| 5,259,972 | 11/1993 | Miyamaru et al. . |
| 5,266,215 | 11/1993 | Englehard . |
| 5,288,412 | 2/1994 | Voorhees et al. . |
| 5,290,439 | 3/1994 | Buchwald . |
| 5,292,585 | 3/1994 | Cox . |
| 5,304,302 | 4/1994 | Bossert .................................... 210/222 |
| 5,326,389 | 7/1994 | Cambon . |
| 5,368,724 | 11/1994 | Ayers et al. . |
| 5,376,281 | 12/1994 | Safta ....................... 210/748 |
| 5,380,445 | 1/1995 | Rivard et al. ........................... 210/748 |
| 5,384,032 | 1/1995 | de Souza ................ 210/104 |
| 5,393,417 | 2/1995 | Cox ........................................ 210/96.1 |
| 5,466,367 | 11/1995 | Coate et al. . |
| 5,466,425 | 11/1995 | Adams ................ 422/186.3 |

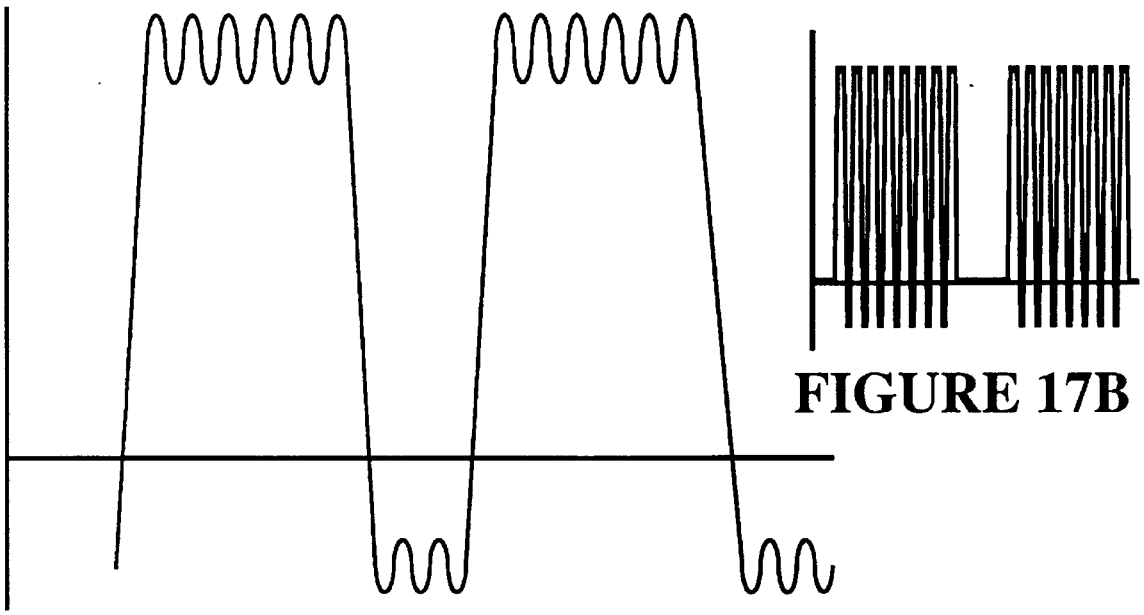
FIGURE 17B
FIGURE 17A
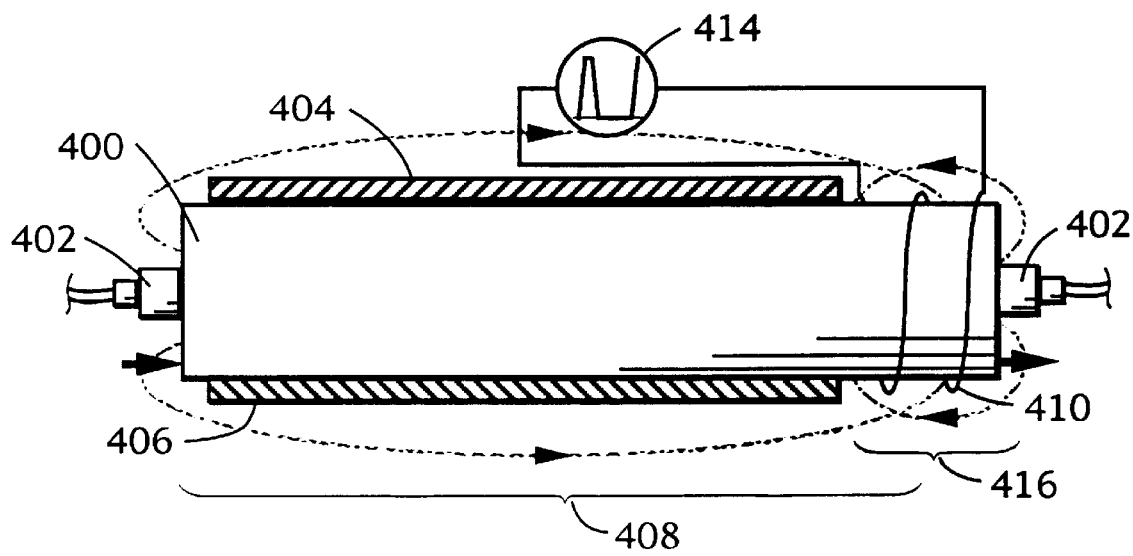
FIGURE 18

DECONTAMINATION SYSTEM WITH IMPROVED COMPONENTS

This application is a Continuation-in-Part of U.S. Patent application Ser. No. 08/273,102, filed Jul. 8, 1994, now U.S. Pat. No. 5,466,425.

BACKGROUND OF THE INVENTION

Since the 19th Century discovery of the cause of cholera epidemics in London and their prevention through treatment of sewage and other effluent to remove and/or kill organisms within the effluent, many advances have been made in the treatment of organically polluted effluent. Early in the development of water treatment systems, chlorine and other halides were found to have deleterious effects on water born organisms, and chlorine compounds are now commonly used to reduce the number of living organisms in water supplies to reasonably safe levels.

It has also been determined that photonic absorption, such as is possible with high levels of radiation at preferentially absorbed frequencies, can cause total photodynamic inactivation of several bacteriophages. (See R. Hall as cited in General Electric Lamp bulletin LD-14; and M. Luckiesh, "Germicidal Eythermal Energy Research" from D. Van Nostrand Co). When a non-fluorescing organism absorbs a photon, the energy is usually converted into vibrational energy (heat) that raises the internal temperature of the organism. Viral organisms are extremely sensitive to such energy. They are so small that the absorption of very few photons causes their internal temperature to rise to levels that are dangerous to their continued existence. In fact, this form of heat energy within viral organisms, causes viral inactivation when the temperatures there within exceed 100° C.

Photobiologists have discovered absorption curves for various biological parts. For example, proteins normally have peak absorption when exposed to radiated ultraviolet (UV) energy at wavelengths of 300 nanometers (nm) to 280 nm, and ribonucleic acid (RNA) has an absorption peak to radiant wavelengths from 265 nm to 245 nm, with an absolute peak at 253.7 nm. The peak absorption for virions occurs at about 260 nm. 184.9 nm energy is the peak energy used for the breakdown of the hydrogen bond that links the DNA chain and phosphorous bond that links the RNA chain. In addition, application of 184.9 nm UV causes free oxygen molecules in the substance under treatment to add an oxygen atom to form ozone, a proven virion deactivator.

Therefore, sterilizers have been constructed that expose a fluid stream to ultraviolet radiation in the 300 nm to 180 nm wavelength range at an applied power of the 30 Kergs per $mm^2$ or more required to disassociate the deoxyribonucleic acid (DNA) and RNA of viral organisms.

Although with prior art UV sterilization devices, it has been possible to provide UV energy in the correct range of wavelengths and at lethal power levels, such UV devices have had numerous disadvantageous features. First, many have poorly designed flow channels that allow organisms to flow there through without receiving a lethal dose of ultraviolet radiation. Most apply the requisite amount of UV too slowly, thereby allowing viral organisms to produce pigment like molecules that dilute the effect of UV light so that what should be a lethal level, can be withstood. Studies have shown that certain types of viral organisms can produce the UV blocking molecules in as little as ten milliseconds. This means that to apply a lethal dose of UV energy to those virions capable of protecting themselves from UV light, enormous concentrations of UV energy must be provided, since a lethal or at least a debilitating amount of UV energy must be applied and absorbed by every exposed viral organism in less than the first ten milliseconds that the viral organism is exposed. Commercially available intense UV sources used in the prior art devices tend to be narrow frequency devices that are unable to produce lethal intensity at all the peak absorption wavelengths of organisms. The broadband UV energy producing devices that are available produce UV light at relatively low power levels. Examples of these latter sources are UV fluorescent tubes, which produce UV at such low levels that literally hundreds of thousands of lamps are required to treat the effluent in a normal commercial sewage treatment plant.

Over time, when selective kills are attempted, either by chemical means, or inadequate levels or improper wavelengths of radiant energy, microorganisms adapt and become resistant to common killing schemes. Hence, in the case of chlorine, there is evidence that sewer and water supply microorganisms have evolved to tolerate high levels of chlorine. In fact, some now even are able to metabolize chlorine. Not withstanding a reduction in efficacy, chemicals like chlorine build up in an environment, if not poisoning it, changing it in undesirable ways.

Therefore, there has been a need to provide a non-chemical microorganism sterilization process and system for performing the process that allows less than one viable microorganism (including bacteria, virions, fungi, and bacterial spores) to pass therethrough, which can be manufactured relatively economically, and can operate in highly polluted, organic waste water environments as well as being scalable to portable potable water supplies at one extreme and to large city sewage treatment systems at the other extreme.

SUMMARY OF THE INVENTION

The present water treatment system, whether it be large enough for the treatment of an entire city's sewer outflow or just large enough to produce potable water for a military platoon size water supply, includes a particulate filter or settling and floating device to remove relatively large solids, greases and other compounds from the input effluent stream that could dirty and clog downstream components of the system. If potable water is to be the final result of the system, chemical filters are included downstream of the solids filters to remove hazardous inorganic materials such as heavy metals from the input stream. Even after passing through fine filters, an effluent stream is likely to have so many bacteria, bacterial spores, fungi and virions therein, that such effluent can be characterized as an organic soup.

The present invention includes a pulse type pump that moves a predetermined amount of this organic soup into a stunning chamber. In the stunning chamber, a relatively high electric potential is applied across bacterial organisms and spores to fracture cell membranes and slow the natural processes of any viral organisms present.

A typical stunning chamber for a sewer treatment plant includes a plurality of interleaved plates of opposite electrical potential that are spaced far enough apart that microorganisms or small organic or inorganic particles do not wedge there between, clogging the chamber, yet close enough to apply substantial electric potential from end to end across bacteria therebetween. If proper levels of electrical potential are applied in the stunning chamber, no celled organisms emerge therefrom with their cell walls intact. Even if the electric potential is insufficient to cause some of the bacteria to lose structural integrity, it can still be large enough to disorient both the viral organisms living therein and virions present in the fluid so that they are unable to initiate their UV protection mechanisms discussed above.

Intense UV light can be applied immediately after stunning to destroy any viral organisms within or outside the bacteria and the spores through photon absorption and thermal destruction. However, in the present water treatment system, the stunned organisms are usually passed first through a cavitation chamber where they are physically agitated for further disorientation and membrane rupture before exposure to UV radiation. A typical cavitation chamber is one having piezo-electric transducers positioned with respect to the flow to assure that all microorganisms passing therethrough are exposed to high levels of acoustic energy (usually greater than 140 dB at 500 to 1000 Hz).

Whether acoustically tortured or not, the microorganisms in the flow are then pulse flowed to one or more molecularly implanted simulated emitter (MISE) chambers usually provided in tubular form to apply high levels of radiant UV energy to the stream without warning to microorganisms in the pulsed stream. The occasional application of very rapid reversals of a relatively intense magnetic field to the microorganisms while they are being pulse flowed within the MISE chambers may be included for an optional enhancement. Rapid reversals of an intense magnetic field has been shown to prevent any fast recovering virion from recovering its UV protection ability, to cause disruption or distorting of protein molecules therein that makes them unavailable for use by the virion, and allows an increase in possible throughput with a fixed amount of power applied to the UV energy source by assuring a kill with fewer applications of UV energy and by increasing the efficiency of mercury vapor UV lamps to which the magnetic field is also applied. Although in large systems, initial exposure to the UV energy may not be sufficient to kill all viral organisms, it at least further inhibits the viral organisms' ability to mount a defense to lethal doses applied over time thereafter. This "surprise" application is accomplished by sizing the flow passages from the pulse pump to the MISE tube and the flow passages within the stunning and cavitation chambers large enough that pulse flow is maintained with little pressure drop. The outlet of the MISE entry tube usually takes the form of a restrictive orifice. Therefor, the flow produced by the pulse pump moves pulse after pulse of fluid into the MISE tube. The pump is coordinated with MISE tube UV exciter control electronics so the MISE entry tube is dark as a fresh volume of effluent is pumped therein. Once the flow has substantially slowed, the magnetic field is reversed and the UV emitter means of the MISE tube are pulsed at high power levels. Since the viral organisms entering the MISE tube have been stunned and tortured until they are unable to use their UV protection mechanisms and damaged by the magnetic field reversals within the MISE tube, in the present system it is not mandatory as otherwise would be the case, that the viral organisms are "surprised" by their exposure to UV energy.

Generally, the MISE tubes are elongated non-magnetic cylinders. Large industrial MISE tubes for sewer treatment have intense UV sources at each end while MISE tubes for portable potable water supplies can include a concentric UV emitter, such as a fluorescent lamp, extending from end to end down the middle thereof. The MISE tubes are designed to expose any microorganism therein to intense UV radiation. One method to assure complete exposure this is to coat the inner surface of the MISE tube with material that is highly reflective of UV radiation. Magnesium oxide is a preferred material because it is easy and economical to apply and is highly reflective of the UV energy. The inner surface is then coated with a UV transparent, protective coating for a long life. Since UV sources seldom produce all of the desired wavelengths of enough intensity, UV fluorescent material that absorb wavelengths in over abundance or those having little affectivity and then re-radiate UV at needed wavelengths otherwise weakly present, may be included in the protective coating. Having the outer wall of the tube actually radiate as well as reflect further assures that within the MISE tube, there is no shadow area where microorganisms can hide. A fast reversing power supply connected to an electric coil spirally wrapped about the cylindrical outer surface of the MISE tube is used to produce the intense magnetic field reversals with in the MISE tube.

Usually, the outlet of the MISE tube is the minimal flow area for the system so that upstream of the MISE tube outlet, effluent flow is in pressure pulses and downstream it is relatively constant flow. The area around the outlet may be coated with compounds that fluoresce at wavelengths that repel microorganisms, since experiments have shown that a small fractional percent of slightly viable, large mobile virion, were attempting to escape from the outlet.

When the area of the MISE tube adjacent the outlet is Gamma soured and bright blue fluoresced, such virion appear to expend enough energy in moving away from the outlet to become deactivated. Therefore, the natural tendencies of such virion to attempt to avoid UV exposure is used against them and the possibility of outlet escape is eliminated. Suitable electronics coordinate the action of the pump, the stunning chamber, the cavitation chamber, and the MISE tube to efficiently use electrical energy supplied thereto to keep operating costs for electrical power to a minimum. The electronics can be programmed to operate independently or can be controlled through the use of operating personnel control inputs and a display.

Tests of small scale versions of the present system show the synergistic effect of both the MISE tube and stunning chamber because if either is not operating, live organisms emerge whereas if both are operating, less than one live organism ever emerges from the MISE tube. However, the effluent flowing out of the MISE tube may be what can be characterized as a primordial life mixture, full of organic molecules and fragments in such concentrations that it is conceivable they could recombine into viable organisms.

In the case of a small scale water supply system, the output is likely to have relatively few organic molecules therein because normally, the input chosen is not highly concentrated raw sewage. Therefore, the small water supply system output may be just passed to a dark solid state chiller so that little energy is available for recombination of the organic molecules and fragments. Although the output water of the chiller is safe to drink, the organic fragments therein tend to preferentially pass yellow optical frequencies, which give the water an unpalatable appearance. Therefore, the output of the chiller is passed through a carbon filter to remove the organic molecules and fragments so that crystal clear drinking water is delivered.

In a sewage treatment system, multiple settling and float tanks, particulate filters, pumps, stunning chambers, cavitation chambers and MISE tubes may be interconnected by suitable valves so that any component can be taken off line for repair or cleaning, should such be required. The output flow of the MISE tubes without further treatment is suitable as the exhaust effluent of a sewage plant. However, since in most instances sewage plants have their output flow piped a considerable distance before being dumped in a diluting water volume (such as a lake, large river or ocean) a flow channel is provided with a covering that either prevents recombination energy from reaching the organic molecules and fragments, or includes a solar filter that allows only damaging radiation to pass into the flow channel to assure no recombination can occur before dilution where the physical distance between the organic molecules and fragments becomes so large that recombination can not occur.

Therefore, it is a principal object of the present invention to provide a non-chemical fluid treatment system for sterilizing a waste water flow.

Another object is to provide a process to treat waste water, which allows less than one organism to pass viably therethrough, and therefore presents no danger of assisting microorganisms to evolve that are resistant to the system.

Another object is to provide an energy efficient microorganism sterilizing method whose operating principles can be applied to small scale potable water supply systems or large sewage treatment plants.

Another object is to provide a UV microorganism sterilizing device having pre-treatment means that overcome viral organism's responsive defenses to UV radiation.

Another object is to provide a MISE tube, which produces high levels of broadband UV radiation suitable for disrupting the nucleic acids of microorganisms and designed so that any organism passing therethrough is exposed to a lethal dose of UV radiation.

Another object is to provide MISE tubes that are long lasting, easily manufactured, and relatively economical to manufacture and operate in a wide variety of environments.

These and other objects and advantages of the present invention will become apparent to those skilled in the art after considering the following detailed specification together with accompanying drawings wherein:

BRIEF DESCRIPTION OF THE DRAWINGS

FIG. 17A is a graph showing the an magnified view of the output of the generator of FIG. 16;

FIG. 17B is a graph illustrating two entire cycles of the generator of FIG. 16;

FIG. 18 is a side elevational view of a modified MISE tube including permanent magnets to generate a magnetic field and a coil to generate a varying magnetic field used to vary the permanent magnetic field.

DETAILED DESCRIPTION OF THE SHOWN EMBODIMENTS

Figure 1:
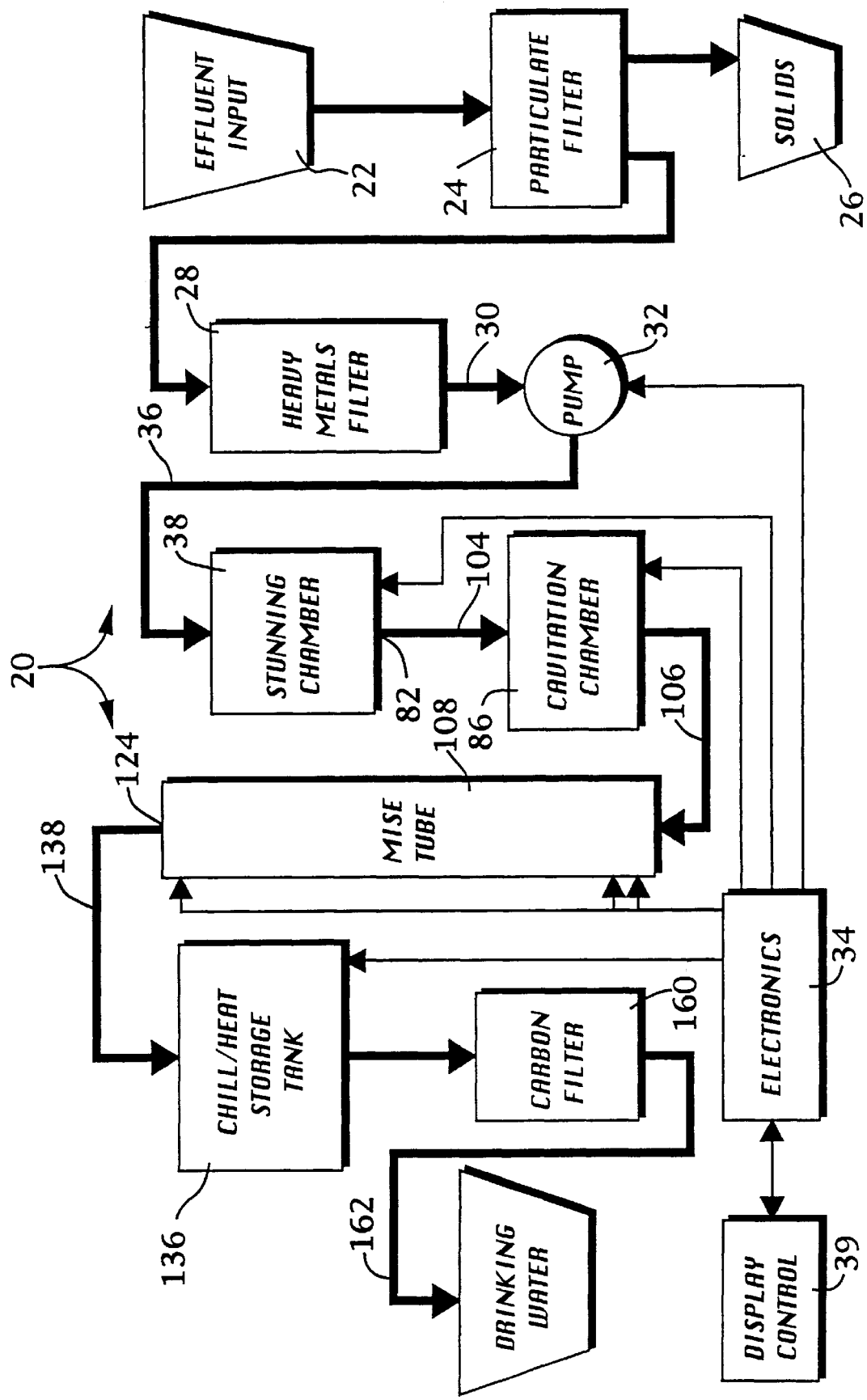
FIG. 1 is a schematic diagram of the present invention as embodied in a small scale potable water supply system.

Referring to the drawings more particularly by reference numbers, number 20 in FIG. 1 refers to a water treatment system for producing drinking water from a affluent input 22 of water of an unknown pollution level. In the system 20 the input 22 may be everything to questionably potable water to a combination of raw sewage and pond scum. Therefore, the input 22 is passed through a particulate filter 24 to remove larger solids primarily to keep them from clogging the flow passages within the system 20. This separates the solids 26 from the water flow. Filter 24 can be any of a number of commercially available filters including a Crane model 1-09-450 filter.

Many input water streams are polluted with other than organic contaminants. Therefore, means such a heavy metals filter or other devices commonly used to remove inorganic contaminants is provided. The output flow 30 from the heavy metals filter 28 provides the input to the organic decontamination portion of the system 20.

The flow 30 is provided as an input to a pump 32. In most instances, the pump 32 is automatically controlled by suitable electronics 34 to produce pulses of fluid flow on its output line 36. Typically, the electronics 38 provides power to the pump on two second intervals. These pulses of flow are input to a stunning chamber 38. A operator control/display 39 can be used to adjust the electronics for different circumstances, or when purging and/or cleaning of the system 30 is required.

Figure 2:
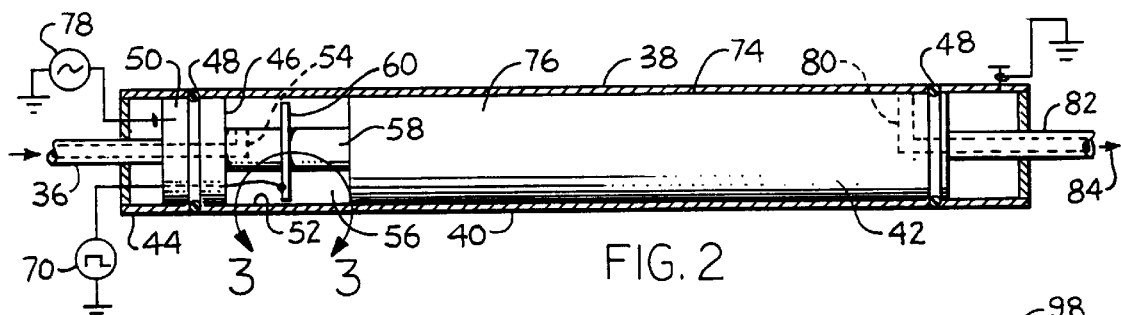
FIG. 2 is a partial cross-sectional view of the stunning chamber of FIG. 1.
Figure 3:
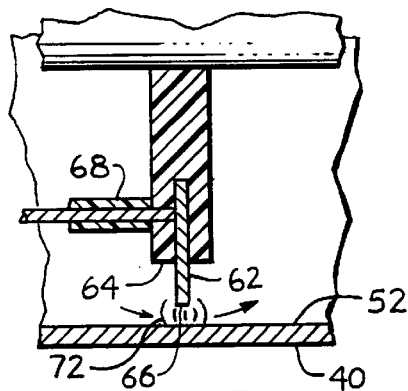
FIG. 3 is an enlarged detail view of the area indicated by the line 3—3 in FIG. 2.
Figure 4:
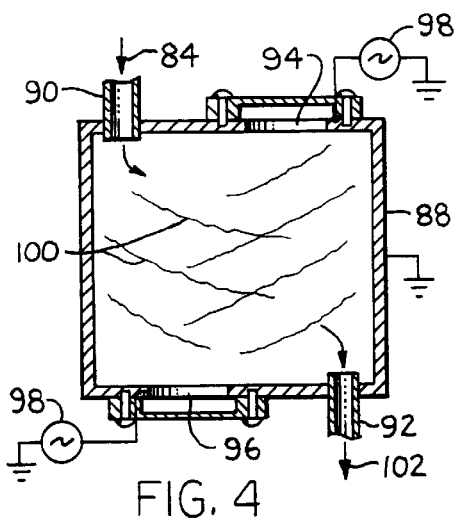
FIG. 4 is a cross-sectional view of the cavitation chamber of FIG. 1.

The stunning chamber 38 is used to break membranes of celled organisms and bacterial spores within the flow to expose any viral organisms there within which otherwise might be able to hide or be shadowed by cellular structures. The details of a stunning chamber 38 suitable for small flows is shown in FIG. 2.

The stunning chamber 38 preferably is constructed from materials that are resistant to corrosion such as stainless steel. The chamber 38 includes an outer tube 40 within which is positioned a cylindrical center body 42 as shown at the input end 44. The center body 42 includes a connection to the output line 36 from the pump 32. The center body 42 includes a blocking disc 46 that includes a seal 48 about its periphery 50. The seal 48 is electrically insulated and so secure that even virions cannot pass there past either against the periphery 50 of the blocking disc 46 or the inner surface 52 of the tube 40.

The center body 42 includes an input passageway 54 forming a flow passage from the output line 36 into an interior stunning chamber 56 formed by a radially cut out portion of the center body 42 so that a reduced diameter portion 58 is formed.

An insulated disc 60 is mounted on the reduced diameter section 58 of the center body 42. The disc includes a conductive ring 62 about its outer radial periphery 64, the ring 62 having an outer edge 66 closely adjacent the inner surface 52 of the tube 40. The conductive ring is connected by means of a conductor 68 to a source of high voltage pulses 70. As shown, the conductor 68 is sealably passed through the blocking disc 46, however it may be run other places that can provide a fluid tight, electrically isolated passage.

As can be seen in FIG. 3, when the high voltage source 70 is on, a high voltage electric field 72 is established between the inner surface 52 the tube 40, which is shown in FIG. 2 as being grounded, and the outer radial surface 66 of the ring 62. All flow through the passageway 54 is pumped through the area of the electric field 72 which may be left on continuously or only applied when the pump 32 is forcing a pulse of flow there past. The disc ring 62 forms a high energy corona point that is very efficient in applying high potential to adjacent organisms, allowing the system 20 to be operated under battery power. Downstream of the disk ring 62, the center body 42 defines a thin concentric tubular passageway 74 between the inner surface 52 of the tube 40 and an cylindrical surface 76. The center body 42 is connected to a high voltage source 78 of alternating current from the electronics 34. The front outer edge 77 of the cylindrical surface 76 preferably is sharply formed to create a second corona point through which all of organisms present in the flow must pass. The passageway 74 has a thickness large enough to allow the largest virion to pass through but small enough to block an intact cell. Since any blocked intact cellular organism will provide a current path between the inner surface 42 and the cylindrical surface 76, its membranes are very quickly destroyed. To prevent bacteria from passing there through, the thickness of the passageway 74 should be about 254 microns and when bacterial spores are a problem, the thickness of the passageway 74 should be reduced to about 127 micrometers with an increase in diameter to keep the flow resistance thereof at about the same level. The passageway 74 is typically made about 100 millimeters long and is driven at a high enough alternating current to cause nucleic acid ionization as well as general thermal deactivation in the one second minimal time that any organism will spend therein. Alternating current is used to prevent the deterioration of the tube 40 that might occur if direct current was used and to cause viral disorientation. Since the passages in the stunning chamber 38 are small, the flow velocity is very high there through, when compared to flow rates in the components downstream thereof, to be discussed hereinafter.

When the structural membranes of cellular organisms are fractured, their contents, including viral organisms, are dumped into the flow which then passes through the narrow concentric passageway 74 formed between the inner surface 52 of the tube 40 and the outer cylindrical surface 76 of the center body 42 down stream-of the interior stunning chamber 56. This breaking of membranes causes the internal nucleic acids of the organisms to also be dumped in the flow causing it to go acidic, which is desirable as an acidic environment is "unfriendly" to most naturally occurring organisms. A second internal passageway 80 connects the passage 74 to the outlet 82 of the stunning chamber 38. The flow 84 therefrom is acidic and contains few, if any, intact cellular organisms or spores and all the virions remaining are in a disoriented and stunned condition where their ability to manufacture UV protective molecules is disrupted.

As an extra precaution to make sure that celled organisms do not survive intact and to provide a cleaning mechanism, the flow 84 then may be passed through a cavitation chamber 86 whose operation is also controlled by the electronics 34. The cavitation chamber 86, whose detail is shown in FIG. 4, includes a water tight housing 88 with an input connection 90 and an output connection 92 attached thereto for flow communication. Piezo electric diaphragms 94 and 96 are positioned facing each other in the housing 88 and are driven by a suitable signal generator 98 in the electronics 38 to produce high intensity acoustic waves 100 that combine in the chamber 86 to produce cavitation in the water there about. The cavitation chamber 86 preferably is made from high silicon stainless steel, such as type 314. This grade of steel is very resistant to water corrosion and due to its almost 50% nickel and chromium composition, it is easy to clean by sonic techniques. The physical dimensions of the cavitation chamber 36 are chosen to optimize the acoustic pressures there within and also so the pressure waves created therein combine in phase at the inlet 90 and outlet 92 for transmission along resonant piping to help keep other components of the system 20 clean and the organisms in the piping disoriented. The acoustic waves 100 are preferably in the frequency bands from 500 to 1000 Hz and from 50 to 70 KHz, since acoustic waves 100 are relatively easy to generate at those frequencies with sufficient intensity to disrupt the membrane of any organism able to withstand the stunning chamber 38. Frequencies at 500 to 1000 Hz are also suitable for resonant matching of the piping lengths required to connect adjacent components for sonic cleaning action. For example, since the velocity of sound in water is about 1430 to 1493 meters per second depending on the temperature, a suitable chamber length for operation at about 733 Hz is about 63.3 nm. The sixth harmonic of longitudinal resonance frequency of a $63.3\times10^{-3}$ m piezo-electric diaphragm equals 71.1 KHz, which provides large separation of the cleaning and cavitation signals.

The diaphragms 94 and 96 can be standard off the shelf, piezo speakers. When the signal generator 98 is connected to the diaphragms 94 and 96 so they are driven in opposite directions with the same signal, the greatest possible pressure differentials appear centrally within the chamber 86. Normally, the signal generators 98 are incorporated within the electronics 34 and may be turned on and off to correspond to pulses of the pump 32.

The connecting piping 104 from the stunning chamber 38 to the cavitation chamber 86 and the connecting dark piping 106 from the cavitation chamber 86 to a molecularly implanted simulated emitter (MISE) tube 108 are about 4 meters in length (about one half of the wave length at 750 Hz) to resonantly couple the acoustic energy of the cavitation chamber 86 therethrough for sonic cleaning of the stunning chamber 38 and the MISE tube 108. The piping 104 and 106, the stunning chamber 38 and the cavitation chamber 86 are made of materials that do not transmit light to literally keep any organisms leaving the stunning chamber 38 in the dark until they reach the MISE tube 108.

Photoprotection is a phenomenon in which irradiation by near UV decreases the sensitivity of certain cells to the UV wavelengths used in the system 20. This protection process is an acquired pigment like plating that reduces the internal UV absorption. To effect a UV shock, the effluent should come from the dark. Within the system 20, a flow delay in the dark piping 104 and 106, and the cavitation chamber 86 is incorporated causing about 10 seconds of time in total desensitizing energy.

Figure 5:
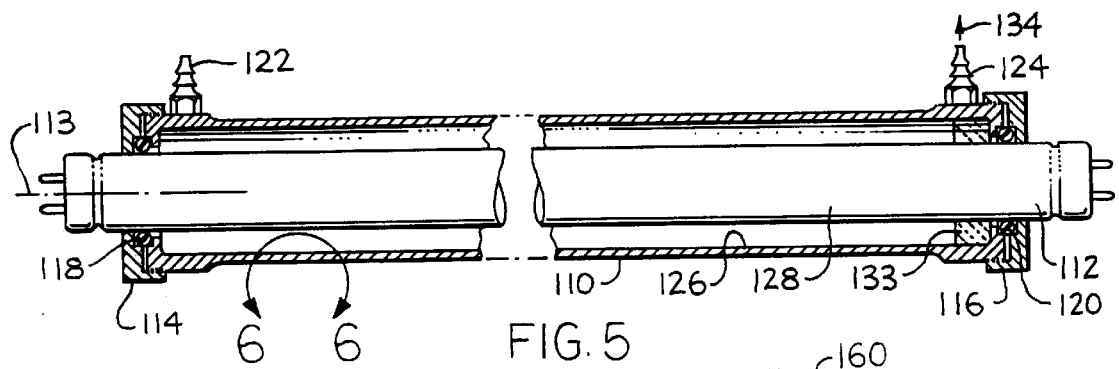
FIG. 5 is a partial cross-sectional view of the MISE tube of FIG. 1.
Figure 6:
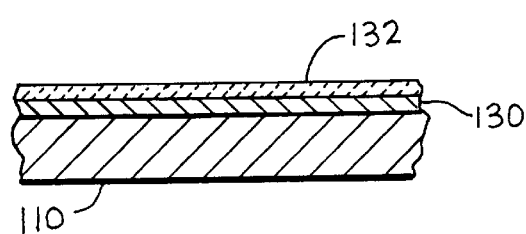
FIG. 6 is an enlarged detail view of the area indicated by the line 6—6 in FIG. 6.

The details of the MISE tube 108 are shown in FIGS. 5 and 6. The MISE tube 108 includes a tubular housing 110 retaining a UV lamp 112 concentrically therein along its longitudinal axis 113 by means of end caps 114 and 116, which in combination with the housing 110 entrap suitable seals 118 and 120 against the UV lamp 112. Preferably, the MISE tube housing 110 is constructed of high silica aluminum extruded tubing. The housing 110 includes an inlet port 122 and an outlet port 124, and with the lamp 112 defines a tubular flow passage 125 through which the pulse flow is maintained. The lamp 112 can be any suitable, off the shelf, low pressure mercury vapor lamp. However, most commercially available power supplies for such lamps are designed on the assumption that lamps driven continuously thereby will be convectively air cooled and continuously driven, and do not allow exploitation of the full UV capabilities of such lamps when they are water cooled and have less than a 100% duty cycle. Therefore the electronics 34 can be designed to provide higher voltage and currents to the UV lamp 112 than is normal practice to cause a more intense sterilizing UV output to be produced. Because of the MISE tube's cylindrical shape, centered lamp 112 and the reflectivity of the tubes inner surface 126, there are only fractional intensity losses. As an example, off-the-shelf circuits and techniques using a germicidal 18 inch lamp only produce about 3.6 watts of 253.7 nm radiation. Therefore, a specialized lamp driver circuit in the electronics 34 is used accounting for a total working 15.6 watts of 253.7 nm flux (15.6 watts is left after some energy is absorbed for fluorescence).

The inner surface 126 of the housing 110 is concentric to the outer surface 128 of the lamp 112 so that no matter what path an organism travels in the tubular flow passage 125 from the inlet 122 to the outlet 124, it is exposed to a lethal dose of UV. To further assure this occurs the inner surface 126, as shown in FIG. 6, includes a highly reflective coating 130 such as magnesium oxide. The reflective coating 130 is covered with a protective coating 132 that includes dopants that absorb UV at the characteristic wavelengths of the mercury lamp 112 and reradiate UV energy at other wavelengths to fill in the UV spectrum produced within the MISE tube 108. Other dopants (such as phosphors) are activated by the alternating potential differences between the plasma in the lamp 112 and the housing 110 to fill in the UV spectrum. Suitable dopants in the MISE coating include: anthranilic acid; benzamidine hyctrochloride; bensene-m- sodium disulfonate; O-chlorobenzoic acid; diphenyl; diphenylanine; hexamethylenetramine triguaiacol; hydrobenzoin; p-phenetole sulfonic acid; and theobromine. UV at 225 nm is needed for virus absorption, UV at 228 nm is needed for pinworms, UV at 253.7 nm is needed for absorption by nucleic acids and UV at 184.9 nm is needed for oxygen and hydrogen bond ionization.

The following process produces a suitable highly reflective inner surface 126 for the housing 110.

After cutting to length and deburring, at least the inner surfaces is smoothed with soft steel wool. The housing 110 is then connected at one end to a positively charged conductive rotator and dipped into a 65° to 72° C. cleaning solution of:

15% Sodium Gluconate $HOCH_2[CH(OH)]_4CO_2$
45% Sodium Hydroxide NaOH
40% Distilled Water $H_2O$ For 2.5 minutes the housing 110 is fully submerged and rotated at 200 RPM. The process is then halted, the housing 110 reversed end-to-end and then the process is continued for another 2.5 minutes. The housing 110 is then removed from solution and washed in Ethyl Alcohol. To achieve a high degree of UV reflectivity, a thin film of molecularly bonded magnesium is then plated onto the inner surface 126 of the housing 110 by mixing a solution of magnesium gluconate in a Pyrex plating tank of the following ingredients:

60% Magnesium Gluconate $\{HOCH_2[CH(CH(OH)]_2CO_2\}Mg*xH_2O$
29% Ammonium Chloride $NH_4Cl$
4.5% Ammonium Thiocyanate $NH_4SCN$
5% Magnesium Turnings Mg
1.5% Erbium (III) Oxide $Er_2O_3$ A diluted solution of ethyl alcohol is saturated at 26° C. with this mixture and an anode of magnesium rod is submerged into the solution. Except for the inner surface 126, the housing 110 is externally coated with a liquid tape, electrically connected to a rotating cathode, and then completely submerged into the solution. The anode is spaced from the housing 110. While rotating at a 200 RPM speed, a current is applied between the anode and the housing 110. A slight occasional current reversal is used to strengthen the bond of the plated magnesium to the aluminum inner surface 126. The temperature is maintained at 26° C. The plating process is continued until the interior diameter of the inner surface 126 has decreased by 25$\mu$m. The finished inner surface 126 is then polished with a soft cotton cloth saturated with the following mixture:

60% PEEK
30% Hexamethylenetramine
5% Dimthylxanthine
5% Diphenylamine

Allowing the tube never to dry by adding ethyl alcohol, the mixture is rubbed over the interior plating for 30 seconds rotating the cloth at a rate of 200 RPM. A clean dry soft cotton cloth is then spun through the tube interior at a rate of 1750 RPM for 30 seconds to cause friction heating, polishing to harden the coating. At this time the ends of the finished housing 110 are capped with metal tape ready for its completion at least 24 hours later.

Figure 7:
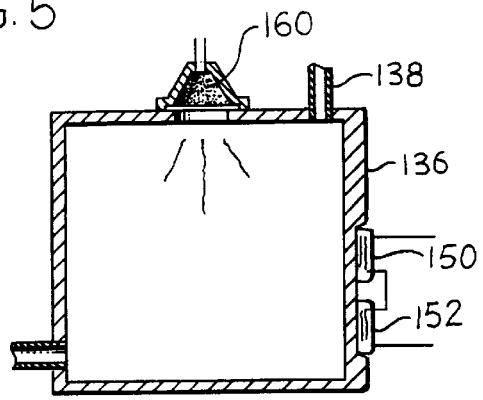
FIG. 7 is a cross-sectional view of the chill/heat storage tank of FIG. 1.

Others have determined that total Photodynamic inactivation of several bacteriophages starts at 30 Kergs/mm$^2$ near 253.7 nm radiation by R. Hull (as cited in General Electric Lamp bulletin LD-14. Also see M. Luckiesh, "Germicidal Eythermal Energy Research" from D. Van Nostrand Co. Apparently this inactivation is caused by photonic absorption forcing the generation of interferons, the cellular proteins produced in response to some stimuli that act to prevent replication of an infectious viral form. When a substance absorbs a photon, the energy is usually converted into mostly vibrational energy (non- fluorescing compounds). This form of "heat energy" will cause inactivation in most viral organisms when allowed to reach 100° C. As shown in FIG. 7, photobiologists have plotted absorption curves for the various biological parts: protein has a peak from 300 nm to 280 nm; and RNA absorption occurs from 245nm to 265 nm with a maximum absorption at 253.7 nm. The general virus absorption peaks at about 260 nm. As a result of this data for inactivation, the MISE tube 108 is designed to deliver a fairly flat intensity of U.V. radiation from 300 nm to 180 nm with a peak output of 253.7 nm.

Having an energy equivalency of $1\times 10^7$ ergs for one joule equaling one watt/sec. and the requirement of 30 Kergs per $mm^2$ for interferon generation resulting in inactivation, a minimum U.V. requirement is calculated to be 3 mJ per $mm^2$.

The MISE tube 108, is a cylindrically contained, bi-directional UV generator with tuned electro-photo-luminescing ability. The MISE tube 108 is designed to hold a volume of effluent solution in close proximity between a UVB (300 to 200 nm germicidal) and UVC (200 to 40 nm ionizing) generator (the lamp 112) and a greater than 97% reflective wall surface 126 with a UVA luminescent coating (400 to 300 nm) that is pumped, yielding an increased reflected UV spectrum.

The required UV energy is dependent on experimentally tested total surface area illumination from both wall and lamp surface. For an 18 inches low pressure mercury lamp, the active output energy is: 355.6 mm of the lamp length. 25.4 mm is the external lamp diameter therefore the total surface area πdh is:

$$\pi(25.4\text{ mm})\ (355.6\text{ mm})=28.38\times103\text{ mm}^2$$

A minimum of 30,000 ergs are required per square mm so:

$$(28.38\times10^3)\ (30\times10^3)=851.24\times10^6$$

at $1\times10^7$ ergs $J^{-1}$ then:

$$\frac{851.24\times10^6\text{ ergs}}{1\times10^7\text{ J}}=85.1\text{ Js}$$

The emitting/reflected surface is also 355.6 mm in length but it is 38.1 mm in diameter so:

$$\pi(38.1\text{ mm})\ (355.6\text{ mm})=42.56\times10^3\text{mm}^2=127.7\text{ Js}$$

A total bi-directional illumination is therefore 212.8 Joule. Hence a measured 15.6 watt delivery system requires a time factor of:

$$\frac{212.8\text{ Js}}{15.6\text{ W}}\text{ or 13.6 seconds}$$

By utilizing an on/off pulsed pump filling from the gravity bottom of the MISE tube 108, a very even, minimum turbidity flow of effluent is accomplished that allows a minimum time of 14 seconds of fluid throughput, as set by experiments for each system 20.

Several photo-physics laboratories have shown that viral buoyancy exists in some virion causing them to float in water. It has also been shown that active virion will migrate away from the blue light portion of the spectrum. Therefore, a specially positioned and enhanced blue fluorescence repeller 133 is included about the general proximity of the outlet 124 of the MISE tube 108 in its protective coating 132. Using the already self contained high photonic energies to cause fluorescence, the blue fluorescence repeller 133 made of a ceramic fluorescent "repeller" consisting of the following weight percents:

| | | |
|---|---|---|
| $CaF_2$ | Fluorspar | 40.00% |
| $U^{238}$ | Uranium | 34.00% |
| LiF | Lithium Fluoride | 15.00% |
| BaO | Barium Oxide | 5.79% |
| $B(OH)_3$ | Boric Acid | 5.00% |

-continued

| | | |
|---|---|---|
| Er | Erbium | .20% |
| Eu | Europium | .01% | emits blue 460 nm light. Along with this fluorescing repeller 133, the outlet 124 is made to be the smallest flow passage so that the flow therethrough regulates the total through-put of fluid of the system 20.

Since the electrical pumping must be alternating currents to pass their effects through the dielectric barriers to the MISE tube 108, pumping frequencies produced are chosen to cause resonant chamber cleaning and also to be physically damaging to virion. RNA, DNA and proteins strongly absorb vibrational energy in the range from 34 KHz to 103 Khz. Therefore a constant virion harmonic amplitude of 69 KHz is superimposed onto the lower cleaning frequency of the cavitation chamber 86 at 733 hertz. This chamber frequency generated in the electronics 34 and applied by the piezo diaphragms 94 and 96 can be controlled to match physical changes in chamber manufacture.

Total required harmonic input energy is based on a maximum virion volume of 28 nm at $6.64\times10-^2$ Kg each.

$$\text{Chamber Volume}=\frac{\pi C}{4}(D^2-d^2)$$

$$V=\frac{\pi(355.6\text{ mm})}{4}(38.1\text{ mm})^2-(25.4\text{ mm})^2$$

For virion approximation:

$$\frac{225.23\times10^3\text{ mm }3}{28\times10^9}$$

$$\text{Count: }\approx8.04\times10^{12}$$

$$\text{Mass: }\approx53.43\text{ ng}$$

and since they are for the most part water, the total energy to generate an 80° C. increase is:

$$53.43\text{ ng}\times80^\circ\approx4.27\times10^6$$

$$(5\times10^3)\ (.2389\text{ J})=1.19\text{ KJs}$$

$$\frac{1.19\text{ KJs}}{13.6\text{ s}}=87.47\text{ watts}$$

Less the already 15.6 watts of UV absorbed, the necessary 71.87 watts of vibrational energy are left.

The transit time within the MISE tube 108 and UV intensities and frequencies therein are chosen to assure that no viable organism passes out of the output 124 thereof in the output flow 134. However, the flow 134 is a variable mix of organic fragments and molecules that theoretically could recombine into viable organisms if the proper environment and energy is provided. Therefore, the flow 134 is directed to a chill/heat storage tank 136 by means of a dark pipe 138. The details of the chill/heat storage tank 136 are shown in FIG. 8. To eliminate the possibility that the organic fragments and molecules will recombine into viable organisms within the tank 136, the chill/heat storage tank 136 includes Peltier cooling diodes 150 and 152, thermally attached to the tank 136 for clean, quiet chilling. The Peltier cooling diode 150 and 152 can be used to cool the water stored in the tank 136 or by using the control 39 to reverse the polarity of the current from the electronics 34, they can also be used to heat the water so hot water is available. A long wavelength infrared (IR) source 154 may be included to provide damaging IR radiation into the tank 136 and an ozone generator 156 also may be provided. The IR source 154 is used to irradiate the flow within the storage tank with long wave length IR, which along with ozone produced by the ozone generator 156, disables any repair enzymes and provides a hostile environment to any wandering microbe by forcing oxidation.

Figure 8:
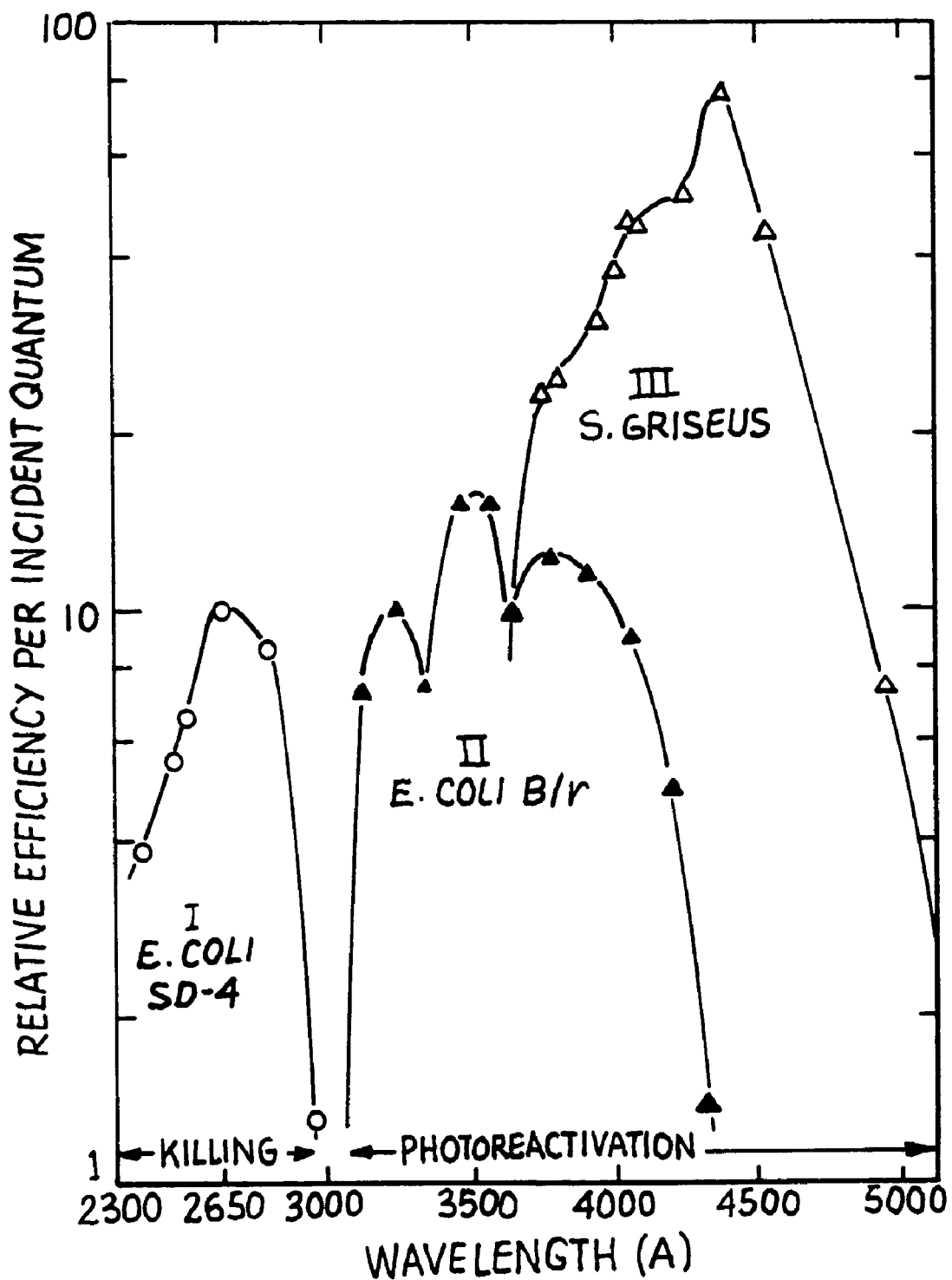
FIG. 8 is a graph of known photoreaction in relation to wavelength and relative efficiency.
Figure 9:
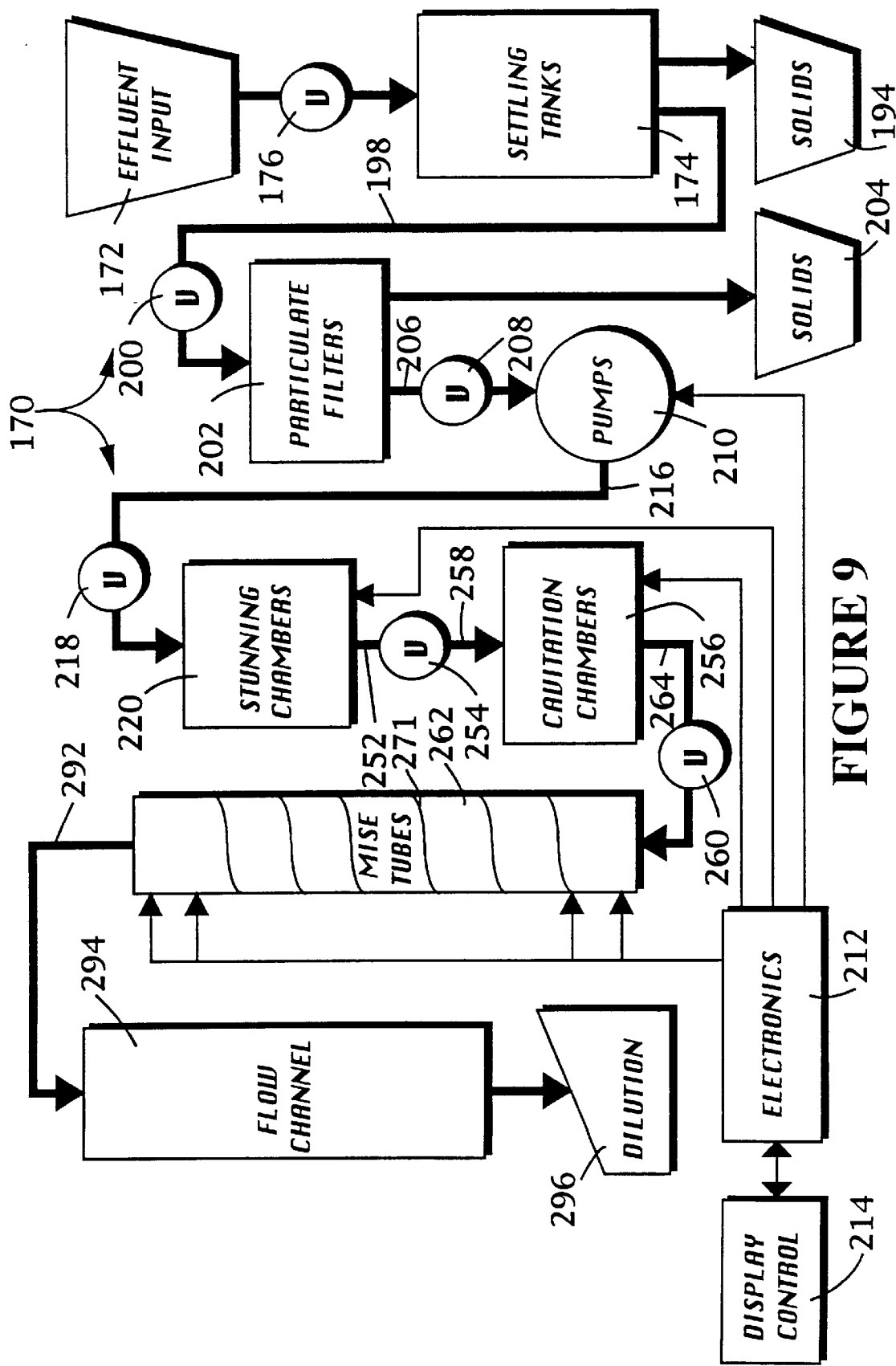
FIG. 9 is a schematic diagram of the present invention as embodied in a large scale sewage treatment facility.

After microbe tissue damage that is not completely fatal, a process called photoreactivation can take place. Photoreactivation of bacterial viruses is temperature and energy dependent. This recovery from damage is enhanced by nutrients, warmer waters and radiation in the 300 to 500 nm range as shown in the example graph of FIG. 8 from existing literature. The impingement of the infrared light from the IR source 154 in the pulsed mode can been used to inhibit the enzyme work without appreciable water heating.

The process of microbe inactivation leaves organic fragments and molecules in the water that scatter and absorb different frequencies of light, which usually cause the water appear amber. Psychologically, amber colored water is not particularly palatable and therefore the water from the tank 136 is flowed through a fine carbon filter 160 capable of removing the small organic bits. Such filters are commercially available and usually are filled with activated carbon. Activated carbon is a large surface granular non-crystallized carbon made by low temperature and low pressure techniques so that it has an enormous number of nanometer pores that can capture and absorb non-polar substances. The output 162 of the carbon filter 160 is suitable for use as drinking water.

A one second pump cycle with suitable flow rate can maintain a suitable discharge pressure to assure the ~14 second UV MISE tube time. In the experimental example described above, effective ⅛ by ½ inch output restriction is a composite restriction, working with the back pressure of the carbon filter 160, and only occurs after the water reaches the filter 160. Therefore, if the system 20 is designed to be very efficient to prevent the wasting of energy, it should be primed slowly to make sure that early high flow rates can not sweep viable virions therethrough.

FIG. 9 is a flow diagram of a large scale waste water treatment system 170. The effluent input 172 to such system 170 typically is raw sewage. The effluent is switched between various settling tanks 174 by suitable valves 176, the details of a settling tank 174 being shown in FIG. 10. The effluent input 172 is bottom fed into the tank body 178 preferably surrounded by a virus attractant and xenon kill device 180 such as are known in the art. The tank body 178 is designed to have almost no currents therein allowing sludge to settle to the bottom 181 of the tank body 178 and be removed at a bottom sludge drain 182 by means of a sludge pump 184. Sludge 186 typically is processed by flowing it onto means like the drying belt 188, where the liquid 190 is removed and forced back into the tank 178 by a recycle pump 192. The solids 194 are collected for further processing and disposal. Since some solids float, a sludge scraper 196 is employed about the upper surface of the tank body 178 to gather the floating sludge adding it into the sludge stream 186 for separating as described above. A large percentage of the solids are removed by the settling tanks 174 so that the output flow 198 thereof is relatively clean except for small particles and microorganisms whose density approximates that of water. Valves 200 (shown in FIG. 9) are used to direct the output flow 198 of the settling tanks 174 through one or more particulate filters 202 similar to those used in the system 20 previously described, but larger and adapted for high flow commercial use. Such particulate filters are commercially available. The particulate filters 202 remove fine solids 204 and produce a flow 206 through valves 208 to one or more pumps 210. Preferably, the pumps 210 like those in system 20 are driven by suitable electronics 212 having a display/control 214, so that the flow downstream from the pumps 210, is in pulses. Generally, the pumps 210 produce pulses that are over 10 seconds long. Accounting for the larger size of the downstream components to be discussed hereinafter, the output 216 of the pumps 210 is directed by suitable valves 218 to stunning chambers 220. A suitable industrial stunning chamber 220 for a waste water treatment plant is shown in exploded detail in FIG. 11.

The stunning chamber 220 includes an inlet 222 into a plenum chamber 224, which causes the flow downstream thereof to be relatively evenly created between spaced parallel electrode plates 226 and 228 with the plates 226 and 228 alternating across the chamber 220. The plates 226 are all connected to one electrode 230 while all the plates 228 are connected to another electrode 232. The plates 226 and 228 include seal and insulating areas 234 and 236 at their upper and lower edges respectively so that flow as shown by arrows 238 occurs at right angles between the plates 226 and 228. Any organisms in the flow 238 are exposed to high electric fields, which are created by applying a high voltage potential across the electrodes 230 and 232. The spacing between the plates 226 and 228 is chosen so that no intact cellular microorganism can pass therethrough without contact with at least one plate. Like the stunning chamber 38, stunning chamber 220 breaks the membranes of cellular organisms releasing their interferons and dumping any viral organisms contained therein into the flow 238 for disorientation and disruption of their UV protection mechanisms.

As shown, the stunning chamber 220 includes suitable flanges 240, bolts 242, and insulating spacers 244 to maintain the structural watertight integrity of the chamber 220. As shown in FIG. 12, the stunning chamber 220 may be positioned within an enclosure 246 so that any incidental leaks from the chamber 220 can be collected by a drain 248 and reintroduced into the flow upstream of the pumps 210. Also, as shown in FIG. 12, preferably the stunning chamber 220 is built with a slight upward bias from input 220 to its outlet 250 so that any gases or air transported or generated by the effluent is pumped clear of the plates 226 and 228 by the flow 238 therethrough.

The outlet flow 252 from the stunning chambers 220 is directed by valves 254 to cavitation chambers 256 by means of dark piping 258 which can block any radiant energy from the outside that might allow repair mechanisms of the organisms stunned by the stunning chambers 220, to repair themselves. The cavitation chambers 256 are similar to those described in detail for system 20 with their frequencies adjusted to account for differing resonant line lengths, chamber sizes and flow requirements. Like before, the cavitation chambers 256 are filled with acoustic energy at a cleaning frequency and a destruction frequency. The lower cleaning frequency being resonantly piped to the stunning chambers 220 and through valves 260 to MISE tubes 262 downstream thereof for cleaning and high frequency sound for disruption and disorientation of the microorganisms in the flow. The output 264 of the cavitation chambers 256 is directed by the valves 260 to a plurality of MISE tubes 262. A typical layout of MISE tubes 262, cavitation chambers 256, stunning chambers 220, pumps 210, and particulate filters 202 are shown in FIG. 10 by the modular blocks 270. This modular configuration downstream of the settling tanks 174, allows a module 270 to be taken off line for maintenance or emergency repair, while the remainder of a waste water treatment facility is operated normally.

Figure 10:
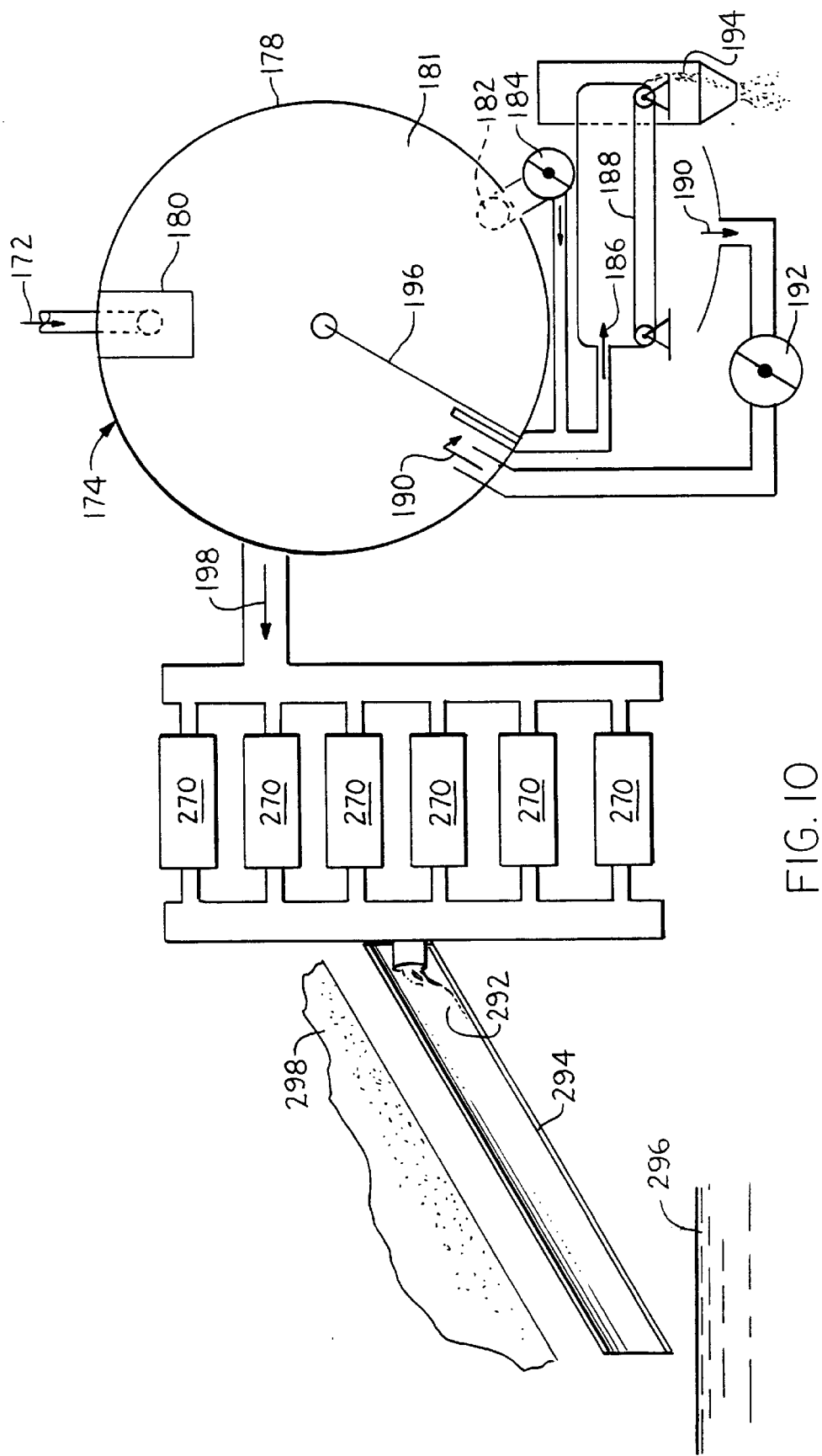
FIG. 10 is another schematic diagram of the present invention as embodied in a large scale sewage treatment facility with the details of a prior art sludge removal tank incorporated therewith.
Figure 11:
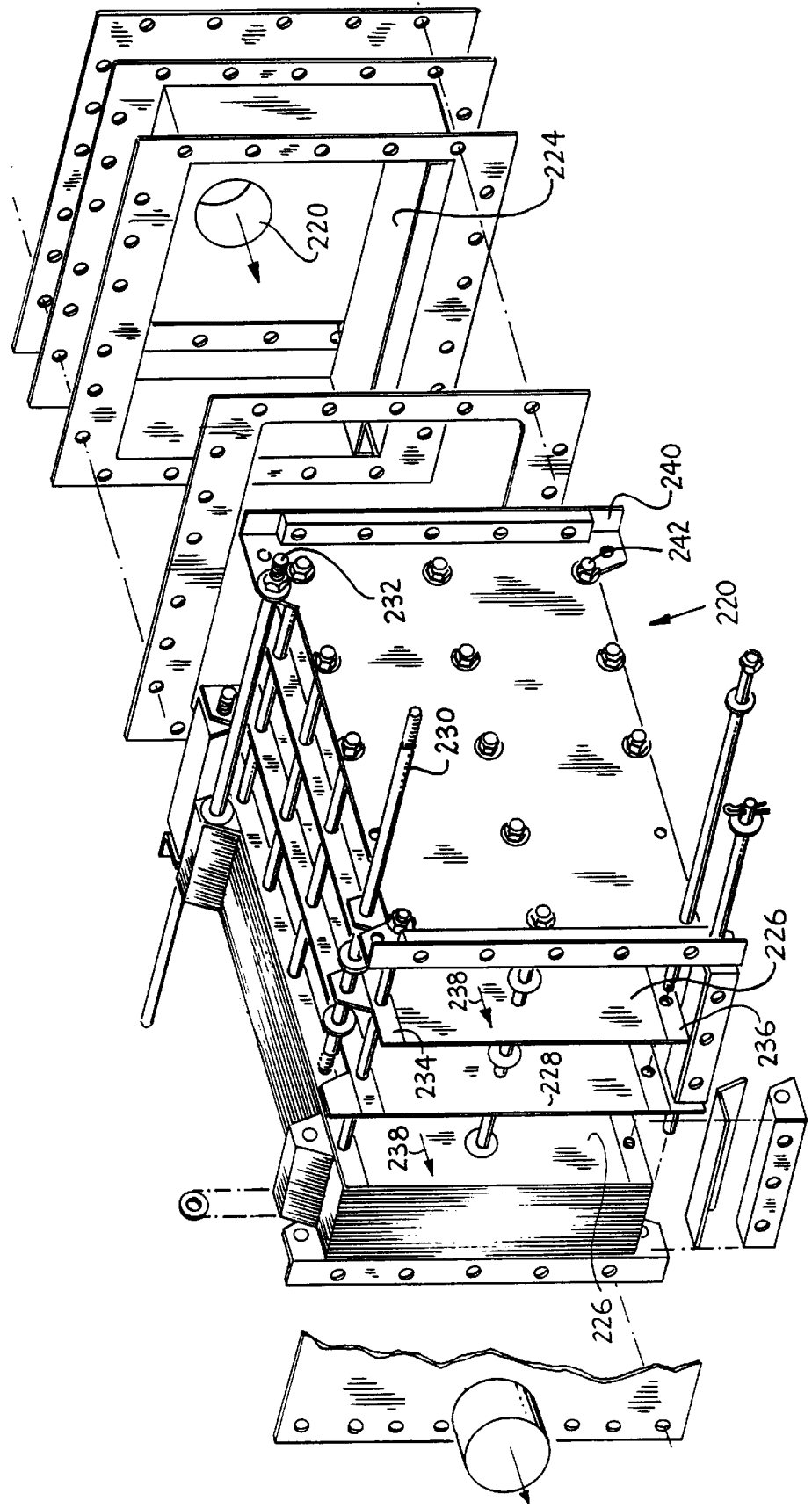
FIG. 11 is an exploded view of a stunning chamber of FIG. 9.
Figure 12:
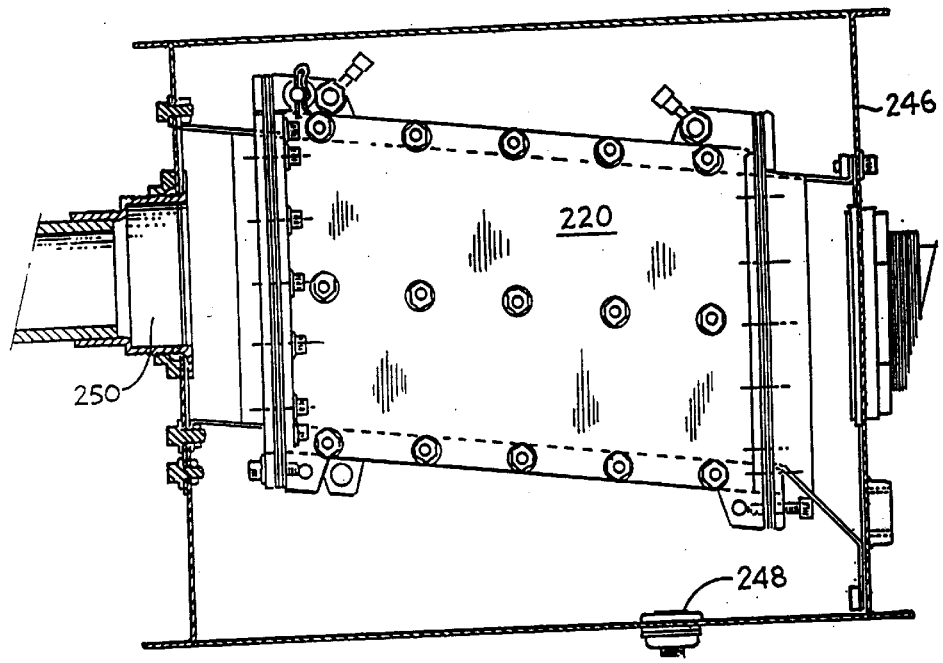
FIG. 12 is a side elevational view of the stunning chamber of FIG. 11 in partial cross-section.

MISE tubes 262 for industrial or waste water treatment facilities must be much larger than those shown in system 20. For example, the plant shown in FIG. 10 might be called upon to have a gravity flow throughput of as much as three million gallons a day, whereas the system 20 might have a maximum throughput of one hundred gallons a day.

Figure 13:
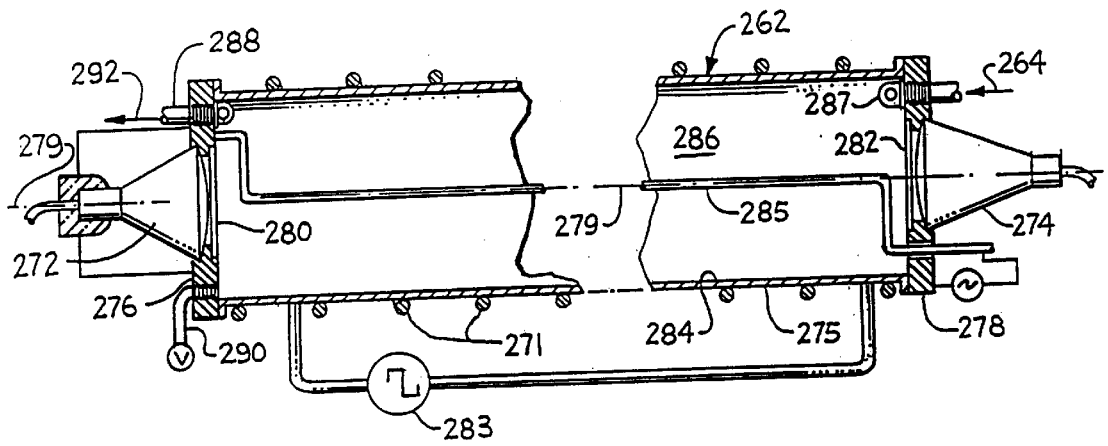
FIG. 13 is a cross-sectional view of the MISE tube of FIG. 9.
Figure 14:
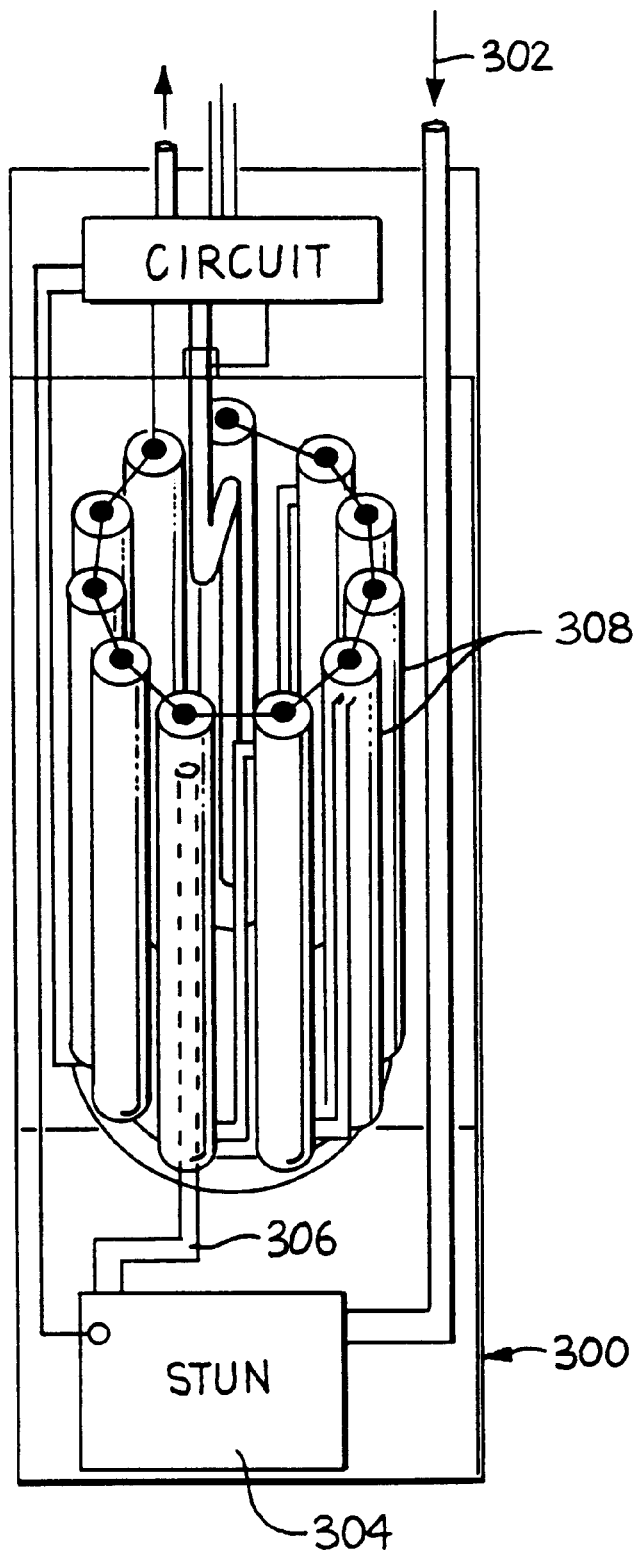
FIG. 14 is a diagrammatic view of a plurality of MISE tubes similar to that of FIG. 5 connected in series for use in an intermediate sized water treatment system.

A typical MISE tube 262 is shown in FIG. 13. The prime difference between the MISE tube 262 and the MISE tube 108 is a matter of scale, the addition of a coil 271 to produce a strong magnetic field within the tube 262, and more intense UV sources such as the mercury lamps 272 and 274 positioned at the opposite ends of a tube housing 275 in opposite end plates 276 and 278 generally centered on the longitudinal axis 279 of the tube 262 behind quartz, sapphire, or other similar heat resistant UV transparent windows 280 and 282. Quartz windows 280 and 282 are preferred because their UV transmission is almost as good as sapphire windows, their cost is low, and their structural strength is high. The strong magnetic field is generally constant with its polarity being switched on about two second intervals by a square wave generator 283. The switching of an intense magnetic field affects microorganisms adversely so that a complete "kill" with UV is more easily accomplished. Generally, the coatings and reflective surfaces of the inside surface 284 of the MISE tube 262 are identical to those of the MISE tube 108.

Other substances that could be substituted to create the effect caused by the incorporation of the ceramic fluorescent "repeller" thereby providing the required deterrent to virion naturally moving to the exit passage of the mise tube to avoid UV exposure, include: hydronzincite; uranium+lithium fluoride; fluorite+europium; andesine+europium; orthoclase+europium; fluorite; benitoite; hydrozincite; margarosanite; scheelite; wolframite+lithium fluoride; allingite; alunogen; amethyst; ceiestite; danburite; diamond diops; dolomite; dumortierite; forsterite; gypsum; hydromagnesite; ktypeite; microcline; opal; pirssonite; plumballophane; simpsonite; and wollastonite.

A centered, highly polished nickel coated and then transparently coated conductor 285 is used in each tube 262 to reflect UV from the longitudinal axis 279 that otherwise would be a wasteful UV "hot spot", to enhance the effectiveness of the MISE tube 262. A 5000 volt alternating current is applied between the conductor 285 and the housing 275 to provide electrons to activate UV producing phosphors in the coating on the inside surface 284 of the MISE tube 262.

The pulse output flow 264 of the cavitation chambers 256 is input into the interior 286 of the tube 262, though an elbow 287 that imparts a swirl thereto to assure that no portion of the flow goes quickly into the outlet 288 and to restrict the line of sight of UV up the flow 264. Note that the outlet 288 faces opposite the swirl to further restrict direct output flow. The flow 264 is subjected to UV radiant energy inside the tube 262 as previously described. Since the UV energy must travel a relatively long distance, the outlet 288 of the MISE tube 262 is sized to be the restriction in the system 270 to assure that any organism remains in the tube 262 for at least 14 seconds so a lethal dose of UV is applied. The 14 second kill time is characteristic of a MISE tube of the dimensions as described above. As shown in FIG. 13, the MISE tube 262 also includes a drain 290 used during maintenance so that the housing 275 can be emptied and thereafter end caps 276 and 278 can be removed from the tube housing 275 without release of sewage.

The outlet flow 292 of the MISE tube 262 usually is gravity flowed in a flow channel 294 to a diluting body of water 296 such as a lake, river or the ocean. The flow channel 294 preferably provides an environment where organic bits are not provided enough energy to recombine into organisms and/or exposes them to destructive radiation, such as when instead of being a black, lightless flow channel, a solar IR filter 298 is provided along the upper surface thereof so that the flow 292 is exposed to damaging IR radiation during the daytime to prevent growth back up the channel toward the MISE tubes 262.

FIG. 14 shows a stun chamber and MISE tube assembly 300 suitable for intermediate flows. The assembly 300 receives an input flow 302 from a suitable pump, the flow 302 being passed through a stunning chamber 304 similar to stunning chamber 220. The output 306 from the stunning chamber 304 is fed serially to a plurality of MISE tubes 308 constructed with the same general configuration as MISE tube 108, but employing commercial UV tubes of the longest length and most intense available. The effect of the series connected MISE tubes 308 is that organisms in the flow 302 are exposed to damaging ultraviolet radiation for a sufficient time to receive a lethal dose even though the velocity flow through the MISE tubes 308 is substantially higher than that found in system 20.

With changing water contaminants passing through the MISE tubes 308, absorption of UV energy can cause severe turbidity in the water, which can effect the amount of UV energy that actually reaches a particular organism. As shown in FIG. 15, the MISE tube 308 can include a centrally located UV sensor 320. By monitoring changes in intensity of the UV energy 322 caused by changes in turbidity, the flow through the MISE tube 308 can be kept at an optimal level. If the contaminated water flowing therethrough gets too UV absorptive and a complete kill is not assured, both a pump 324 on the input line 326 and a valve 328 can be controlled by suitable electronics to reduce flow. As shown, the electronics may include a buffer amplifier 332 connected to the sensor 320. The output 334 of the buffer amplifier 332 is averaged with a reference signal 336 in an averaging amplifier 338 before being converted into frequency modulated pulses in a voltage controlled oscillator 340. The output frequency of the voltage controlled oscillator 340 is converted into a count representative of energy present in the MISE tube 308 at the sensor 320 by a timer 342, which outputs digital counts to a counter/comparator 344 suitably programmed on data lines 345 to produce control outputs on line 346 to a pump controller 348 and on line 350 to a valve controller 352. Normally, the controller 348 will control the pump cycles of the pump 324 while the controller 352 will maintain a desired back pressure in the output 354 by partial closure of the valve 328 to assure that the MISE tube 308 remains full.

The MISE tube 308 can have various configurations of coils to establish magnetic fields therein. For example, in FIG. 16, two coils 360 and 362 connected together with opposite polarity, are energized by a single saw tooth wave generator 364, which produces abrupt reversals of the magnetic fields 366 and 368, respectively. As generally discussed above, the fields 366 and 368 are rapidly reversed and then held over a period of time that interacts with the UV flash lamps 370 and 372 to increase their output and stretches their lower frequency spectrum without incurring an energy penalty. Applying a magnetic field to the gas or vapor atoms within the lamps 370 and 372, increases the efficiency of their production of photons at UV frequencies.

The coil 360 is placed at the input end 374 of the MISE tube 308 to intensely disorient and stress organic bi-radicals.

Organic bi-radicals become paramagnetic during exposure to the high energy photons acquiring a positive magnetic susceptibility. A paramagnetic substance is an assembly of magnetic dipoles that have random orientation, which in the presence of a relatively strong magnetic field have their magnetization vectors determined by the magnetic field. This condenses the magnetic flux lines and therefore the suspended paramagnetic organic radicals condense into the field.

During the absorption of the high energy photons and magnetic flux, atoms become raised in energy level that ordinarily would hamper any further absorption of energy. In order to obtain continuous absorption, it is necessary to provide some method of energy relaxation or else the input energy level will be absorbed inefficiently.

Figure 15:
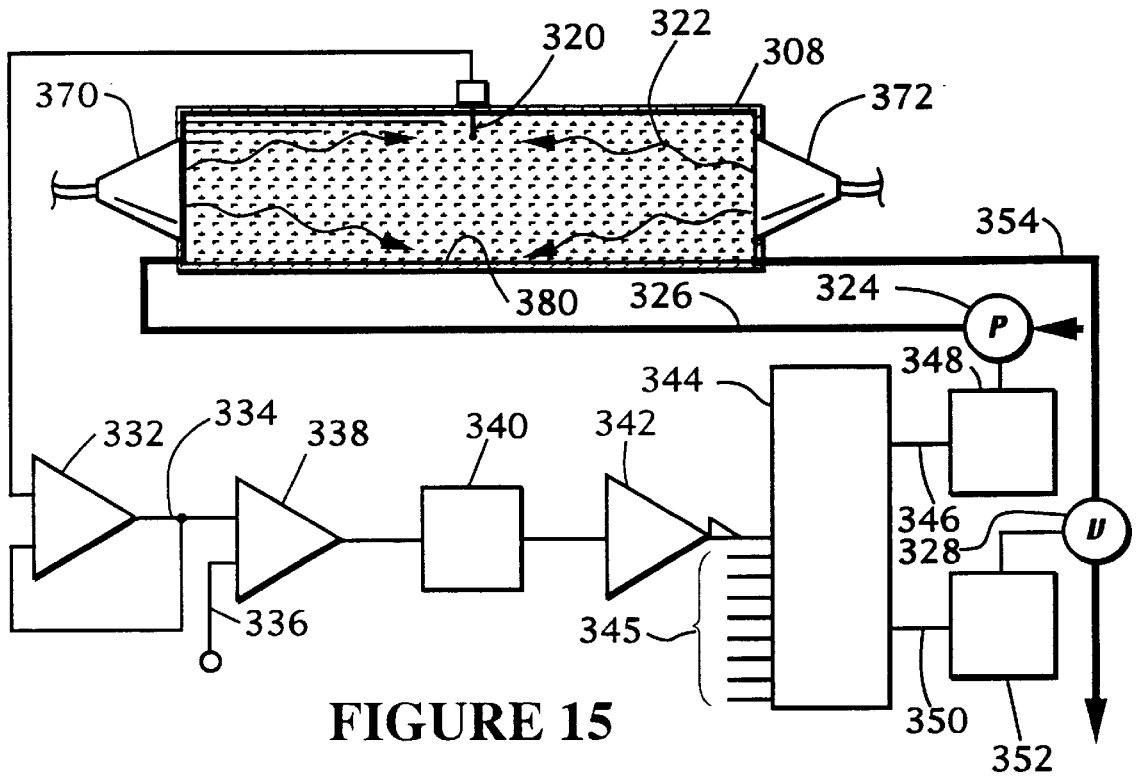
FIG. 15 is a diagrammatic view of a MISE tube control, which varies the flow in response to sensed UV levels in the MISE tube.
Figure 16:
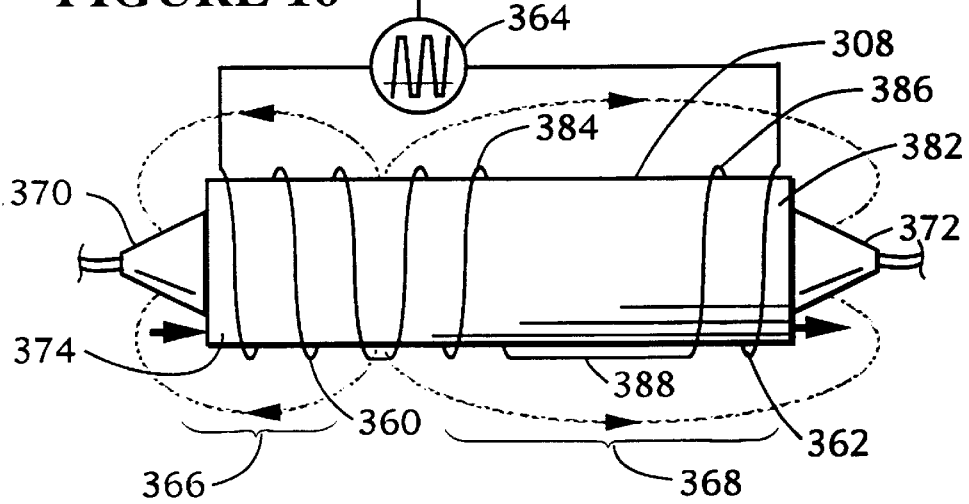
FIG. 16 is a side elevational view of a modified MISE tube including a pair of varying magnetic fields, which increase the efficiency of the UV lamps and assist in the destruction of organisms sensitive to magnetic fields.
Figure 19:
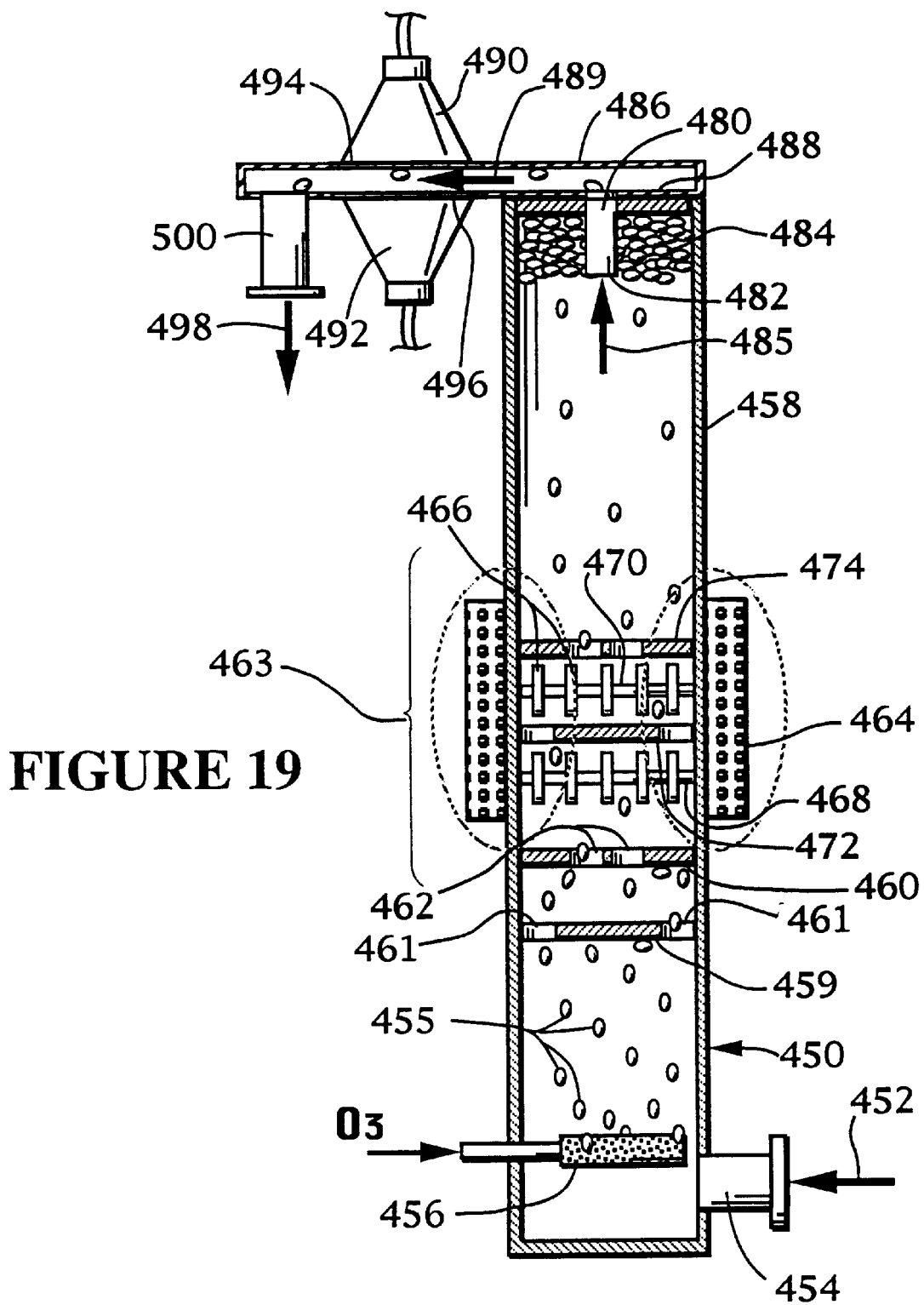
FIG. 19 is a side cross-sectional view of an ozone generator that can be used to inactivate the effluent that flows from a MISE tube.

The inner perimeter 380 (FIG. 15) has the greatest high energy photon count and therefore with a properly placed magnetic field, the biological contaminants can be condensed into this area to increase absorption of energy and act to increase the time of exposure before exiting. If the magnetic field is made to vibrate by adding a high frequency variation from a high frequency generator 381 and reverse by a switched alternating current, then resonant absorption equilibrium never will exist so that continuous magnetizations result. For active biological contaminants, this causes navigational chaos, again increasing the total energy absorbed.

Preferably, the drive energy to the UV generators such as lamps 370 and 372, is made to vary abruptly in correspondence with the variations in the magnetic fields 366 and 368. This allows much higher energy peaks and therefore, greater quantum absorption without excessive power levels in the lamps 370 and 372. A built in side effect of adding the magnetics to the MISE tube 308 is that it holds atoms in their triplet states making recombination repair less probable. FIG. 17A is a graph showing the an magnified view of the output of the generator 364 while FIG. 17B illustrates two entire cycles of the generator 364.

Although the coils 360 and 362 are shown diagramatically, generally the coil 360 can be multiturned and overwound to produce an intense magnetic field 366 at the input end 374 of the MISE tube 308, and to assure efficient output of the lamp 370. Thereafter, down the MISE tube toward its outlet end 382, tighter winding portions 384 and 386 are constructed at the opposite ends of the coil 362 with a wider wrap or as shown, no wrap at all in the center section 388 thereof. This maintains a desired flux level along the coil 362 assuring that the lines of flux extend from the coil 360 to the lamp 372. Note the polarity reversal of the fields 366 and 368.

In FIG. 18, a modified, small MISE tube 400 is shown which uses a fluorescent tube 402 extending concentrically through the MISE tube 400 as the UV source. The MISE tube 400 is designed for use when minimal power consumption is desired, such as a portable battery powered system. The MISE tube 400 includes permanent magnets 404 and 406 which establish a magnetic field 408 within the MISE tube 400. A small coil 410 is positioned at the outlet end 412 of the MISE tube 400, which is occasionally energized by the generator 414 to modulate the field 408 by producing a reverse electromagnetic field 416.

Modern regulations require a residual chlorine concentration in potable water, primarily as a proof that a suitable kill concentration once existed in the water. However, the residual chlorine required by most governmental regulations is not sufficient to kill organisms that might invade the water supply downstream of its purification system and the regulations tolerate a certain level of contamination judged to be non-threatening. Although, one of the objects of the present invention is to avoid the use of chlorine, until regulations are changed to recognize that the present devices exist to provide a complete kill, chlorine must be added. There is nothing about the present invention that prevents chlorine from being later added so that the water supply conforms to regulation.

In cases where the broken, organic molecules cannot be diluted to eliminate the chance that they will recombine into viable reproducing molecules, ozone can be added to the effluent flow. The addition of ozone with additional UV energy causes an enhanced binding of the oxygen to the molecules, in what otherwise can be described as a "soup of life", making cellular reconnectivity much more unlikely in uncontrolled conditions after treatment.

FIG. 19 illustrates a mixer device 450 which efficiently mixes ozone with the effluent flow. The treated effluent 452 enters the input 454 of the mixer 450 where it is immediately exposed to a stream of ozone bubbles 455 produced by a porous stone 456 within a vertical column 458. The bubbles of ozone 455 are momentarily retarded in their upward flow by capture plates 459 and 460, which includes out of alignment fluid passages 461 and 462 to cause a circulating action. Intense vibrational motion is created thereabove by an intense varying magnetic field 463 generated by the coil 464, which aids and opposes the field of toroidal ceramic magnets 466 which slide on their mounting shafts 468 and 470. Additional capture plates 472 and 474 above the magnetic mixing toroids assure that the effluent flow is fully saturated with ozone. A vertically aligned tube 480 with its input end 482 extending into the column 458 causes an ozone pocket 484 to form in the effluent flow to allow a large concentration of ozone that can mix in the narrow effluent flow 485 passing through the tube 480. The effluent flow is then passed between narrow passage plates 486 and 488, which convert the flow 485 into a thin flow 489 between UV lamps 490 and 492. The UV lamps 490 and 492 provide unimpeded short wave light through lenses 494 and 496 into the flow 489 without a shadow. This UV energy is used to cause enhanced binding of the oxygen atoms to the broken molecules in the effluent making cellular reconnectivity extremely unlikely no matter what the conditions after the oxygenated effluent 498 leaves the discharge tube 500.

Thus, there has been shown and described novel waste water treatment systems which fulfill all of the objects and advantages sought therefore. Many changes, alterations, modifications and other uses and applications of the subject waste water treatment systems and components will become apparent to those skilled in the art after considering the specification together with the accompanying drawings. All such changes, alterations and modifications which should not depart from the spirit and scope of the invention are deemed to be covered by the invention, which is limited only by the claims that follow:

I claim:

1. A method for sterilizing water in a flow path containing microorganisms comprising the steps of (a) applying an electrical potential across the water flow path of sufficient strength to disable defense mechanisms of the microorganisms in said water to ultraviolet light; and (b) applying a lethal frequency range and power of ultraviolet radiation and a magnetic field across the water flow path, whereby the water in said flow path is sterilized.

2. A method for sterilizing water as defined in claim 1 wherein said application of ultraviolet radiation comprises irradiating at least a portion of said flow path with said ultraviolet radiation.

3. A method for sterilizing water as defined in claim 1, further comprising the step of cavitating the flow path with high frequency acoustic energy prior to applying said ultraviolet radiation and magnetic field.

4. A method for sterilizing water as defined in claim 3, wherein said cavitating step comprises applying low frequency cleaning acoustic energy to the water in said flow path.

5. A method for sterilizing water as defined in claim 1, further comprising pumping the flow path in pulses.

6. A method for sterilizing water as defined in claim 1, further comprising cooling the flow path after applying said ultraviolet radiation and magnetic field.

7. A method for sterilizing water as defined in claim 1, further comprising filtering the flow path after at least one of steps (a) and (b).

8. A method for sterilizing water as defined in claim 1, further comprising irradiating the water in said flow path with infrared energy after applying said ultraviolet radiation and magnetic field.

9. A method for sterilizing water as defined in claim 8, further comprising diluting the flow path with water after applying infrared energy.

10. A method for sterilizing water as defined in claim 1, which comprises treating said flow path with ozone after applying said ultraviolet radiation and magnetic field.

11. A method for sterilizing water in a flow path containing microorganisms comprising the steps of
   (a) applying an electrical potential across the water flow path of sufficient strength to rupture cell membranes and disable defense mechanisms of microorganisms in said water to ultraviolet light; and
   (b) applying a lethal frequency range and power of ultraviolet radiation and a magnetic field across the water flow path, whereby the water in said flow path is sterilized.

12. A method for sterilizing water as defined in claim 11 wherein said application of ultraviolet radiation comprises irradiating at least a portion of said flow path with said ultraviolet radiation.

13. A method for sterilizing water as defined in claim 11, further comprising the step of cavitating the flow path with high frequency acoustic energy prior to applying said ultraviolet radiation and magnetic field.

14. A method for sterilizing water as defined in claim 13, wherein said cavitating step comprises applying low frequency cleaning acoustic energy to the water in said flow path.

15. A method for sterilizing water as defined in claim 11, further comprising pumping the flow path in pulses.

16. A method for sterilizing water as defined in claim 11, further comprising cooling the flow path after applying said ultraviolet radiation and magnetic field.

17. A method for sterilizing water as defined in claim 11, further comprising filtering the flow path after at least one of steps (a) and (b).

18. A method for sterilizing water as defined in claim 11, further comprising irradiating the water in said flow path with infrared energy after applying said ultraviolet radiation and magnetic field.

19. A method for sterilizing water as defined in claim 18, further comprising diluting the flow path after applying infrared energy.

20. A method for sterilizing water as defined in claim 11, further comprising treating said flow path with ozone after applying said ultraviolet radiation and magnetic field.

21. A method for sterilizing water in a flow path containing microorganisms comprising applying to the water in said flow path
   (1) a lethal frequency range and power of ultraviolet radiation; and
   (2) a magnetic field of varying intensity.

22. A system for sterilizing water in a flow path containing microorganisms comprising
   (a) apparatus for applying an electrical potential across the water flow path of sufficient strength to disable defense mechanisms of the microorganisms in said water to ultraviolet light; and
   (b) apparatus for applying a lethal frequency range and power of ultraviolet radiation and an apparatus for supplying a magnetic field across the water flow path.

23. A system for sterilizing water as defined in claim 22 wherein said apparatus for supplying ultraviolet radiation is downstream from said apparatus for applying an electrical potential.

24. A system for sterilizing water as defined in claim 22 wherein said apparatus for supplying a magnetic field is downstream from said apparatus for supplying an electrical potential.

25. A system for sterilizing water as defined in claim 22 wherein said apparatus for supplying ultraviolet radiation and said apparatus for supplying a magnetic field operate simultaneously.

26. A system for sterilizing water as defined in claim 22, further comprising an apparatus for applying high frequency acoustic energy to the water in said flow path, said apparatus being positioned in the flow path upstream from the point at which said ultraviolet radiation and magnetic field are applied across said flow path.

27. A system for sterilizing water as defined in claim 22, further comprising an apparatus to pump the flow path in pulses.

28. A system for sterilizing water as defined in claim 22, further comprising an apparatus for cooling the flow path after applying ultraviolet radiation and the magnetic field.

29. A system for sterilizing water as defined in claim 22, further comprising a filter positioned in the flow path downstream from said electrical potential apparatus.

30. A system for sterilizing water as defined in claim 22, further comprising an apparatus which irradiates the water in said flow path with infrared energy.

31. A system for sterilizing water as defined in claim 22, which comprises an apparatus for supplying ozone to the water in said flow path, said apparatus being positioned downstream from said apparatus to apply said ultraviolet radiation and said magnetic field.

32. A system for sterilizing water in a flow path containing microorganisms comprising
   (a) means to apply an electrical potential across the water flow path of sufficient strength to rupture cell membranes and disable defense mechanisms of microorganisms in said water to ultraviolet light; and
   (b) a first means to apply a lethal frequency range and power of ultraviolet radiation to the water flow path and a second means to apply a magnetic field to the water flow path, wherein said first and second means operate simultaneously.

33. A system for sterilizing water as defined in claim 32, further comprising cavitating means to apply high frequency acoustic energy to the water in the flow path, said cavitating means being positioned in the flow path upstream from said first and second means for applying ultraviolet radiation and magnetic field.

34. A system for sterilizing water as defined in claim 32, further comprising a means to pump the flow path in pulses.

35. A system for sterilizing water as defined in claim 32, further comprising a means to cool the water flow path positioned downstream from said first and second means for applying said ultraviolet radiation and magnetic field.

36. A system for sterilizing water as defined in claim 32, further comprising a filter positioned in the flow path downstream from said means to apply an electrical potential.

37. A system for sterilizing water as defined in claim 32, further comprising means to irradiate the water in said flow path with infrared energy, said irradiating means being positioned in said flow path downstream from said first and second means to apply ultraviolet radiation and magnetic field.

38. A system for sterilizing water as defined in claim 32, further comprising means to treat said flow path with ozone positioned downstream from said first and second means to apply ultraviolet radiation and magnetic field.

39. A system for sterilizing water in a flow path containing microorganisms comprising (1) means for applying a lethal frequency range and power of ultraviolet radiation to the water in said flow path; and (2) means to apply a magnetic field of varying intensity to the water in said flow path.

* * * * *